US009943421B2

(12) United States Patent
Sverrisson et al.

(10) Patent No.: US 9,943,421 B2
(45) Date of Patent: Apr. 17, 2018

(54) MEMBRANE PUMP SYSTEM FOR USE WITH A PROSTHETIC SYSTEM

(71) Applicant: Ossur Iceland ehf, Reykjavik (IS)

(72) Inventors: Atli Orn Sverrisson, Reykjavik (IS); Larus Gunnsteinsson, Reykjavik (IS); Gudfinna Halldorsdottir, Reykjavik (IS); Hafsteinn Jonasson, Reykjavik (IS); Dadi Granz, Reykjavik (IS); Dana Stewart Marlin, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

(21) Appl. No.: 15/161,464

(22) Filed: May 23, 2016

(65) Prior Publication Data

US 2016/0338859 A1    Nov. 24, 2016

Related U.S. Application Data

(60) Provisional application No. 62/164,646, filed on May 21, 2015.

(51) Int. Cl.
*F04B 45/04* (2006.01)
*A61F 2/80* (2006.01)
(Continued)

(52) U.S. Cl.
CPC .................. *A61F 2/80* (2013.01); *A61F 2/60* (2013.01); *F04B 45/04* (2013.01);
(Continued)

(58) Field of Classification Search
CPC .................................................. A61F 2002/802
See application file for complete search history.

(56) References Cited

U.S. PATENT DOCUMENTS 708,685 A    9/1902    White
980,457 A    1/1911    Toles
(Continued)

FOREIGN PATENT DOCUMENTS

AU    670631 B2    7/1996
BE    675 386 A    5/1966
(Continued)

OTHER PUBLICATIONS

Brochure, "Sometimes Less is More, Harmony P3" Otto Bock, 12 pages. Available at, http://www.ottobock.com/cps/rde/xbcr/ob_es/646A303-EN-01-1001w.pdf", dated 2012.
(Continued)

*Primary Examiner* — Jacqueline Woznicki
(74) *Attorney, Agent, or Firm* — Workman Nydegger

(57) ABSTRACT

A vacuum suspension system includes a pump system arranged to be in fluid communication with a prosthetic socket. The pump system includes a pump mechanism having a housing and a membrane situated on the housing such that a fluid chamber is defined between the membrane and the housing. The pump mechanism is movable between an original configuration in which the volume of the fluid chamber is zero or near-zero, and an expanded configuration in which the volume of the fluid chamber is increased.

14 Claims, 9 Drawing Sheets

(51) Int. Cl.
*A61F 2/60* (2006.01)
*A61F 2/66* (2006.01)

(52) U.S. Cl.
CPC . *A61F 2002/607* (2013.01); *A61F 2002/6642* (2013.01); *A61F 2002/6678* (2013.01); *A61F 2002/802* (2013.01)

(56) References Cited

U.S. PATENT DOCUMENTS

| | | |
|---|---|---|
| 1,288,803 A | 12/1918 | Beck |
| 1,586,015 A | 5/1926 | Underwood |
| 2,424,278 A | 7/1947 | Kunkel |
| 2,464,443 A | 3/1949 | Ganoe et al. |
| 2,530,285 A | 11/1950 | Catranis |
| 2,533,404 A | 12/1950 | Sharp et al. |
| 2,606,325 A | 8/1952 | Nielson et al. |
| 2,664,572 A | 1/1954 | Blevens |
| 2,671,225 A | 3/1954 | Schoene et al. |
| 2,696,010 A | 12/1954 | Robinson |
| 2,696,011 A | 12/1954 | Galdik |
| 2,790,180 A | 4/1957 | Hauser |
| 2,808,593 A | 10/1957 | Anderson |
| 3,253,600 A | 5/1966 | Scholl |
| 3,322,873 A | 5/1967 | Hitchcock |
| 3,377,416 A | 4/1968 | Kandel |
| 3,557,387 A | 1/1971 | Ohlenbusch et al. |
| 3,631,542 A | 1/1972 | Potter |
| 3,712,298 A | 1/1973 | Snowdon et al. |
| 3,732,578 A | 5/1973 | Pollack |
| 3,751,733 A | 8/1973 | Fletcher et al. |
| 3,806,958 A | 4/1974 | Gusev |
| 3,858,379 A | 1/1975 | Graves et al. |
| 3,889,301 A | 6/1975 | Bonner, Sr. |
| 3,895,405 A | 7/1975 | Edwards |
| 3,922,727 A | 12/1975 | Bianco |
| 3,947,156 A * | 3/1976 | Becker ................. F04B 43/0054 417/413.1 |
| 3,975,350 A | 8/1976 | Hudgin et al. |
| 3,991,424 A | 11/1976 | Prahl |
| 4,010,052 A | 3/1977 | Edwards |
| 4,106,745 A | 8/1978 | Carrow |
| 4,133,776 A | 1/1979 | Pruett et al. |
| 4,282,325 A | 8/1981 | Rubenstein et al. |
| 4,283,800 A | 8/1981 | Wilson |
| 4,314,398 A | 2/1982 | Pettersson |
| 4,381,768 A | 5/1983 | Erichsen et al. |
| 4,404,296 A | 9/1983 | Schapel |
| 4,456,642 A | 6/1984 | Burgdorfer et al. |
| 4,466,936 A | 8/1984 | Schapel |
| 4,479,272 A | 10/1984 | Beldzidsky |
| 4,623,354 A | 11/1986 | Childress et al. |
| 4,634,446 A | 1/1987 | Kristinsson |
| 4,635,626 A | 1/1987 | Lerman |
| 4,655,779 A | 4/1987 | Janowiak |
| 4,704,129 A | 11/1987 | Massey |
| 4,822,371 A | 4/1989 | Jolly et al. |
| 4,828,325 A | 5/1989 | Brooks |
| 4,888,829 A | 12/1989 | Kleinerman et al. |
| 4,908,037 A | 3/1990 | Ross |
| 4,923,475 A | 5/1990 | Gosthnian et al. |
| 5,007,937 A | 4/1991 | Fishman et al. |
| 5,108,455 A | 4/1992 | Telikicherla |
| 5,108,456 A | 4/1992 | Coonan, III |
| 5,133,776 A | 7/1992 | Crowder |
| 5,139,523 A | 8/1992 | Paton et al. |
| 5,163,965 A | 11/1992 | Rasmusson et al. |
| 5,201,774 A | 4/1993 | Greene |
| 5,211,667 A | 5/1993 | Danforth |
| 5,221,222 A | 6/1993 | Townes |
| 5,258,037 A | 11/1993 | Caspers |
| 5,314,497 A | 5/1994 | Fay et al. |
| 5,353,525 A | 10/1994 | Grim |
| 5,362,834 A | 11/1994 | Schapel et al. |
| 5,376,129 A | 12/1994 | Faulkner et al. |
| 5,376,131 A | 12/1994 | Lenze et al. |
| 5,376,132 A | 12/1994 | Caspers |
| 5,397,628 A | 3/1995 | Crawley et al. |
| 5,405,407 A | 4/1995 | Kodama et al. |
| 5,480,455 A | 1/1996 | Norvell |
| 5,490,537 A | 2/1996 | Hill |
| 5,507,834 A | 4/1996 | Laghi |
| 5,534,034 A | 7/1996 | Caspers |
| 5,549,709 A | 8/1996 | Caspers |
| 5,555,216 A | 9/1996 | Drouot |
| 5,571,208 A | 11/1996 | Caspers |
| 5,593,454 A | 1/1997 | Helmy |
| 5,658,353 A | 8/1997 | Layton |
| 5,658,354 A | 8/1997 | Norvell |
| 5,702,488 A | 12/1997 | Wood et al. |
| 5,702,489 A | 12/1997 | Slemker |
| 5,709,017 A | 1/1998 | Hill |
| 5,728,166 A | 3/1998 | Slemker |
| 5,728,167 A | 3/1998 | Lohmann |
| 5,728,168 A | 3/1998 | Laghi et al. |
| 5,728,169 A | 3/1998 | Norvell |
| 5,728,170 A | 3/1998 | Becker et al. |
| 5,732,578 A | 3/1998 | Kang |
| 5,735,906 A | 4/1998 | Caspers |
| 5,807,303 A | 9/1998 | Bays |
| 5,830,237 A | 11/1998 | Kania |
| 5,846,063 A | 12/1998 | Lakic |
| 5,888,216 A | 3/1999 | Haberman |
| 5,888,230 A | 3/1999 | Helmy |
| 5,888,231 A | 3/1999 | Sandvig et al. |
| 5,904,721 A | 5/1999 | Henry et al. |
| 5,904,722 A | 5/1999 | Caspers |
| 5,931,872 A | 8/1999 | Lohmann |
| 5,944,760 A | 8/1999 | Christensen |
| 5,980,577 A | 11/1999 | Radis et al. |
| 5,984,972 A | 11/1999 | Huston et al. |
| 6,007,582 A | 12/1999 | May |
| 6,063,125 A | 5/2000 | Arbogast et al. |
| 6,066,107 A | 5/2000 | Habermeyer |
| D429,335 S | 8/2000 | Caspers et al. |
| 6,117,117 A | 9/2000 | Mauch |
| 6,149,691 A | 11/2000 | Fay et al. |
| 6,231,616 B1 | 5/2001 | Helmy |
| 6,231,617 B1 | 5/2001 | Fay |
| 6,273,918 B1 | 8/2001 | Yuhasz et al. |
| 6,287,345 B1 | 9/2001 | Slemker et al. |
| 6,296,669 B1 | 10/2001 | Thorn et al. |
| 6,334,876 B1 | 1/2002 | Perkins |
| 6,361,568 B1 | 3/2002 | Hoerner |
| 6,362,387 B1 | 3/2002 | Carlson et al. |
| 6,402,788 B1 | 6/2002 | Wood et al. |
| 6,406,499 B1 | 6/2002 | Kania |
| 6,478,826 B1 | 11/2002 | Phillips et al. |
| 6,508,842 B1 | 1/2003 | Caspers |
| 6,544,292 B1 | 4/2003 | Laghi |
| 6,554,868 B1 | 4/2003 | Caspers |
| 6,589,289 B2 | 7/2003 | Ingimarsson |
| 6,602,295 B1 | 8/2003 | Doddroe et al. |
| 6,613,096 B1 | 9/2003 | Shirvis |
| 6,626,952 B2 | 9/2003 | Janusson et al. |
| 6,645,253 B2 | 11/2003 | Caspers |
| 6,673,117 B1 | 1/2004 | Soss et al. |
| 6,702,858 B2 | 3/2004 | Christensen |
| 6,706,364 B2 | 3/2004 | Janusson et al. |
| 6,726,726 B2 | 4/2004 | Caspers |
| 6,761,742 B2 | 7/2004 | Caspers |
| 6,767,370 B1 | 7/2004 | Mosler et al. |
| 6,797,008 B1 | 9/2004 | Arbogast et al. |
| 6,855,170 B2 | 2/2005 | Gramnas |
| 6,863,695 B2 | 3/2005 | Doddroe et al. |
| 6,926,742 B2 | 8/2005 | Caspers et al. |
| 6,964,688 B1 | 11/2005 | Kania |
| 6,969,408 B2 | 11/2005 | Lecomte et al. |
| 6,974,484 B2 | 12/2005 | Caspers |
| 7,025,792 B2 | 4/2006 | Collier |
| 7,025,793 B2 | 4/2006 | Egilsson |
| 7,371,262 B2 | 5/2008 | Lecomte et al. |
| 7,427,297 B2 | 9/2008 | Patterson et al. |
| 7,448,407 B2 | 11/2008 | Alley et al. |
| 7,468,079 B2 | 12/2008 | Collier |

(56) References Cited

U.S. PATENT DOCUMENTS

| | | |
|---|---|---|
| 7,686,848 B2 | 3/2010 | Christensen |
| 7,744,653 B2 | 6/2010 | Rush et al. |
| 7,909,884 B2 | 3/2011 | Egilsson et al. |
| 7,922,775 B2 | 4/2011 | Caspers |
| 7,947,085 B2 | 5/2011 | Haines et al. |
| 7,993,413 B2 | 8/2011 | Perkins et al. |
| 8,007,543 B2 | 8/2011 | Martin |
| 8,034,120 B2 | 10/2011 | Egilsson et al. |
| 8,052,760 B2 | 11/2011 | Egilsson et al. |
| 8,080,065 B2 | 12/2011 | Scussel et al. |
| 8,097,043 B2 | 1/2012 | Egilsson |
| 8,097,766 B2 | 1/2012 | Carlson et al. |
| 8,114,167 B2 | 2/2012 | Caspers |
| 8,298,294 B2 | 10/2012 | Kaltenborn et al. |
| 8,317,876 B2 | 11/2012 | Mosler |
| 8,343,233 B2 | 1/2013 | Perkins et al. |
| 8,523,951 B2 | 9/2013 | Kania |
| 8,956,422 B2 | 2/2015 | Halldorsson |
| 8,961,618 B2 | 2/2015 | Lecomte et al. |
| 9,044,348 B2 | 6/2015 | Halldorsson et al. |
| 9,072,617 B2 * | 7/2015 | Halldorsson ............... A61F 2/80 |
| 9,198,780 B2 | 12/2015 | Jonsson et al. |
| 9,757,256 B2 * | 9/2017 | Sandahl ................... A61F 2/80 |
| 2001/0005798 A1 | 6/2001 | Caspers |
| 2001/0016781 A1 | 8/2001 | Caspers |
| 2002/0052663 A1 | 5/2002 | Herr et al. |
| 2002/0087215 A1 * | 7/2002 | Caspers ................ A61F 2/5046 623/34 |
| 2002/0091449 A1 | 7/2002 | Caspers et al. |
| 2002/0103545 A1 | 8/2002 | Arbogast et al. |
| 2002/0128580 A1 | 9/2002 | Carlson et al. |
| 2003/0191539 A1 | 10/2003 | Caspers |
| 2004/0024322 A1 | 2/2004 | Caspers |
| 2004/0030411 A1 | 2/2004 | Gaspers |
| 2004/0049290 A1 | 3/2004 | Bedard |
| 2004/0064195 A1 | 4/2004 | Herr |
| 2004/0122528 A1 | 6/2004 | Egilsson |
| 2004/0163278 A1 | 8/2004 | Caspers et al. |
| 2004/0181290 A1 | 9/2004 | Caspers |
| 2004/0236434 A1 | 11/2004 | Carstens |
| 2004/0260403 A1 | 12/2004 | Patterson et al. |
| 2005/0131324 A1 | 6/2005 | Bledsoe |
| 2005/0131549 A1 | 6/2005 | Caspers |
| 2005/0143838 A1 | 6/2005 | Collier |
| 2005/0240282 A1 | 10/2005 | Rush et al. |
| 2005/0267603 A1 | 12/2005 | Lecomte et al. |
| 2006/0074493 A1 | 4/2006 | Bisbee, III et al. |
| 2006/0212130 A1 | 9/2006 | Collier |
| 2006/0212131 A1 | 9/2006 | Curtis |
| 2007/0005149 A1 | 1/2007 | Egilsson et al. |
| 2007/0043316 A1 | 2/2007 | Carlson et al. |
| 2007/0050044 A1 | 3/2007 | Haynes et al. |
| 2007/0055383 A1 | 3/2007 | King |
| 2007/0112440 A1 | 5/2007 | Perkins et al. |
| 2007/0196222 A1 | 8/2007 | Mosler et al. |
| 2007/0204487 A1 | 9/2007 | Clough |
| 2008/0086218 A1 | 4/2008 | Egilsson |
| 2008/0243266 A1 | 10/2008 | Haynes et al. |
| 2008/0269911 A1 | 10/2008 | Street et al. |
| 2008/0269912 A1 | 10/2008 | Gobbers et al. |
| 2009/0036998 A1 | 2/2009 | Finlinson et al. |
| 2009/0132056 A1 | 5/2009 | Kania |
| 2009/0157196 A1 | 6/2009 | Danzig et al. |
| 2009/0198346 A1 | 8/2009 | Perkins et al. |
| 2009/0204229 A1 | 8/2009 | Mosler et al. |
| 2009/0281637 A1 | 11/2009 | Martin |
| 2010/0070051 A1 | 3/2010 | Carstens |
| 2010/0087931 A1 | 4/2010 | Bogue |
| 2010/0106260 A1 | 4/2010 | Phillips |
| 2010/0262261 A1 | 10/2010 | Laghi |
| 2010/0312359 A1 | 12/2010 | Caspers |
| 2010/0312360 A1 | 12/2010 | Caspers |
| 2010/0331749 A1 | 12/2010 | Powaser |
| 2011/0035027 A1 | 2/2011 | McCarthy |
| 2011/0060421 A1 * | 3/2011 | Martin ..................... A61F 2/68 623/34 |
| 2011/0071649 A1 | 3/2011 | McKinney |
| 2011/0087142 A1 | 4/2011 | Ravikumar et al. |
| 2011/0130846 A1 | 6/2011 | Kampas et al. |
| 2011/0184532 A1 | 7/2011 | Tompkins |
| 2011/0202143 A1 | 8/2011 | Caspers |
| 2011/0270413 A1 | 11/2011 | Haynes |
| 2011/0295386 A1 | 12/2011 | Perkins et al. |
| 2012/0000092 A1 | 1/2012 | Ingvarsson et al. |
| 2012/0022667 A1 | 1/2012 | Accinni et al. |
| 2012/0035520 A1 | 2/2012 | Ingimundarson et al. |
| 2012/0123559 A1 | 5/2012 | Mosler et al. |
| 2012/0173000 A1 | 7/2012 | Caspers |
| 2012/0173001 A1 | 7/2012 | Caspers |
| 2012/0191217 A1 | 7/2012 | Mackenzie |
| 2013/0053982 A1 | 2/2013 | Halldorsson |
| 2013/0096694 A1 | 4/2013 | Caldwell et al. |
| 2013/0282142 A1 | 10/2013 | Perkins et al. |
| 2013/0289741 A1 * | 10/2013 | Halldorsson ............... A61F 2/80 623/34 |
| 2014/0249648 A1 | 9/2014 | Sandahl |
| 2016/0120665 A1 | 5/2016 | Muller |
| 2016/0199202 A1 | 7/2016 | Jonasson et al. |

FOREIGN PATENT DOCUMENTS

| | | |
|---|---|---|
| CA | 2 098 945 C | 7/1997 |
| CN | 1946358 A | 4/2007 |
| CN | 1989342 A | 6/2007 |
| CN | 101815870 A | 8/2010 |
| DE | 685 861 C | 12/1939 |
| DE | 745 981 C | 5/1944 |
| DE | 27 12 342 A1 | 9/1977 |
| DE | 27 29 800 A1 | 1/1979 |
| DE | 32 21 920 A1 | 4/1983 |
| DE | 42 17 877 A1 | 12/1992 |
| DE | 43 21 182 C1 | 12/1994 |
| DE | 94 18 210 U1 | 1/1995 |
| DE | 94 19 211 U1 | 2/1995 |
| DE | 94 17 913 U1 | 3/1995 |
| DE | 299 05 020 U1 | 7/1999 |
| DE | 29823435 U1 | 7/1999 |
| EP | 0 019 612 A1 | 11/1980 |
| EP | 0 057 838 A1 | 8/1982 |
| EP | 0 057 839 A1 | 8/1982 |
| EP | 0 086 147 A1 | 8/1983 |
| EP | 0 261 884 A1 | 3/1988 |
| EP | 0 320 170 A1 | 6/1989 |
| EP | 0 363 654 A2 | 4/1990 |
| EP | 0 631 765 A1 | 1/1995 |
| EP | 0 650 708 A1 | 5/1995 |
| EP | 0 870 485 A2 | 10/1998 |
| EP | 1 509 176 A1 | 3/2005 |
| EP | 1 875 881 A1 | 1/2008 |
| EP | 2816978 A1 | 12/2014 |
| FR | 1 135 516 A | 4/1957 |
| FR | 1 532 625 A | 7/1968 |
| FR | 2 420 035 A1 | 10/1979 |
| FR | 2 501 999 A1 | 9/1982 |
| GB | 136 504 A | 12/1919 |
| GB | 267 988 A | 3/1927 |
| GB | 2 069 847 A | 9/1981 |
| GB | 2 149 309 A | 6/1985 |
| JP | H07-155343 A | 6/1995 |
| SE | 88-01686 L | 3/1989 |
| SU | 1667855 A1 | 8/1991 |
| SU | 1771722 A1 | 10/1992 |
| SU | 1812982 A3 | 4/1993 |
| SU | 1821177 A1 | 6/1993 |
| WO | 84/00881 A1 | 3/1984 |
| WO | 95/05792 A1 | 3/1995 |
| WO | 96/21405 A1 | 7/1996 |
| WO | 98/04218 A1 | 2/1998 |
| WO | 98/55055 A1 | 12/1998 |
| WO | 99/05991 A2 | 2/1999 |
| WO | 99/65434 A1 | 12/1999 |
| WO | 00/03665 A1 | 1/2000 |
| WO | 00/74611 A2 | 12/2000 |

(56) References Cited

FOREIGN PATENT DOCUMENTS

| | | | |
|---|---|---|---|
| WO | 01/54631 | A1 | 8/2001 |
| WO | 01/70147 | A2 | 9/2001 |
| WO | 02/26158 | A2 | 4/2002 |
| WO | 02/065958 | A2 | 8/2002 |
| WO | 02/067825 | A2 | 9/2002 |
| WO | 02/080813 | A2 | 10/2002 |
| WO | 03/077797 | A2 | 9/2003 |
| WO | 03/099173 | A1 | 12/2003 |
| WO | 03/099188 | A1 | 12/2003 |
| WO | 2005/039444 | A2 | 5/2005 |
| WO | 2005/105000 | A1 | 11/2005 |
| WO | 2010/141960 | A2 | 12/2010 |
| WO | 2011/035099 | A1 | 3/2011 |
| WO | 2012010309 | A1 | 1/2012 |
| WO | 2014194998 | A1 | 12/2014 |
| WO | 2016112030 | A1 | 7/2016 |

OTHER PUBLICATIONS

Information Guide, "Harmony Users Guide Otto Bock, 9 pages, available at http://media.ottobock.com/Prosthetics/Socket-Technologies/Harmony/_Genreal/Files/12072403.1_OB-Harmony-UsersGuide-9-10-12.pdf", dated 2012.

Brochure,"Harmony Certification Course Manual," Original Harmony Pump, 42 pages. Availiable at, http://academy.ottobockus.com/videos/harmony/data/downloads/harmony%20course%20manual%202013.pdf. Dated 2013.

Brochure, Harmony P2 & HD, 2 pages. Available at http://www.ottobock.com/cps/rde/xchg/ob_us_en/hs.xsl/14904.html?id=4641. Dated 2012.

International Search Report from corresponding International PCT Application No. PCT/US2013/025849, dated Jun. 4, 2013.

International Search Report and Written Opinion from corresponding International PCT Application No. PCT/US2013/038668, dated Aug. 7, 2013.

Haberman, Louis J., "Silicone-Only Suspension (SOS) with Socket-Loc and the Ring for the Lower Limb", found at, http://www.oandp.org/jpo/library/1995_01_002.asp. Journal of Prosthetics and Orthotics 1995; vol. 7, No. 1, p. 2, 19 pages, dated 2012.

International Search Report and Written Opinion from corresponding International PCT Application No. PCT/US2014/019218, dated May 9, 2014.

International Search Report from PCT Application No. PCT/US2015/044434, dated Oct. 8, 2015.

International Search Report from PCT Application No. PCT/US2015/041089, dated Oct. 5, 2015.

International Search Report from corresponding PCT Application No. PCT/US2016/033915, dated Jul. 29, 2016.

International Search Report from PCT Application No. PCT/US2016/012215, dated May 23, 2016.

International Search Report from PCT Application No. PCT/US2016/033707, dated Jul. 29, 2016.

International Search Report from PCT Application No. PCT/US2017/048354, dated Nov. 16, 2017.

* cited by examiner

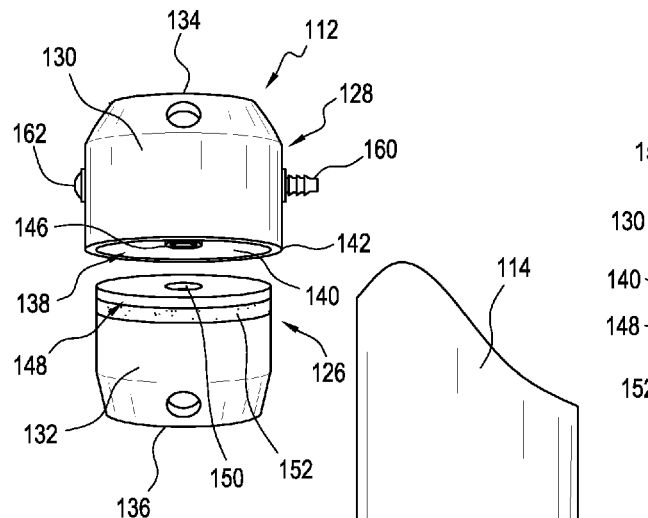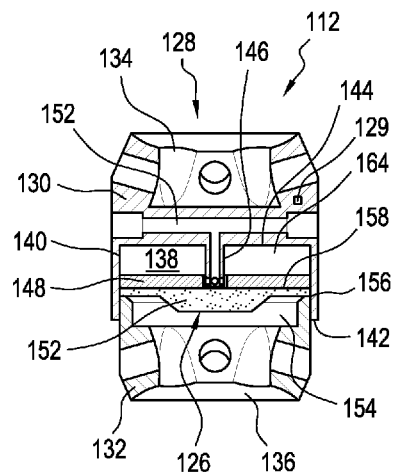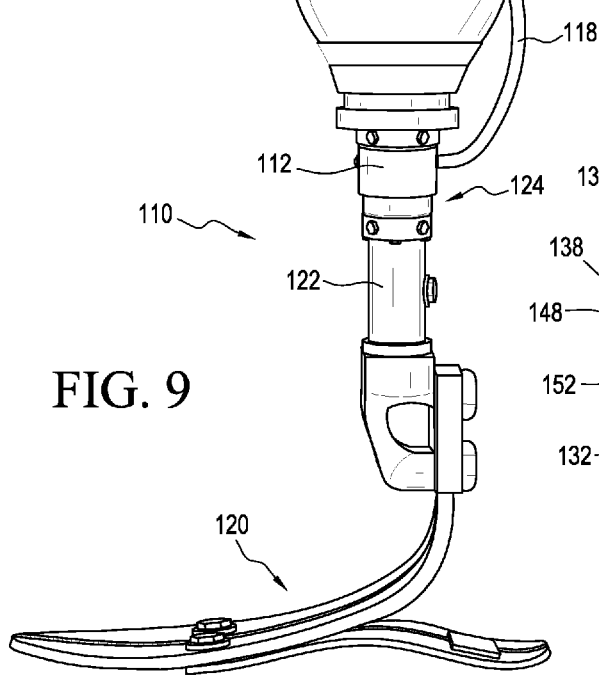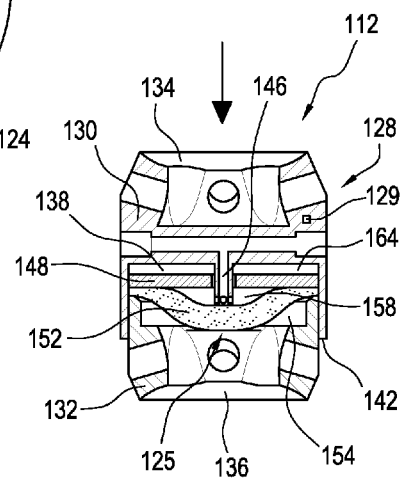
FIG. 10
FIG. 11
FIG. 9
FIG. 12

MEMBRANE PUMP SYSTEM FOR USE WITH A PROSTHETIC SYSTEM

TECHNICAL FIELD

The disclosure relates to the field of prosthetic devices, and more particularly to a prosthetic device, system and pump mechanism for increasing vacuum in a vacuum assisted suspension system.

BACKGROUND

An ongoing challenge in the development of prosthetic devices is the attachment of the prosthetic device to the residual limb of a user. For prosthetic legs, it is often difficult to securely attach the prosthetic leg to the residual leg without exerting too much or uneven pressure on the residual limb. On the one hand, the lack of a secure attachment can adversely affect the user's ability to walk. On the other hand, an improper fit can cause sores, swelling and pain for the user.

One approach for overcoming this challenge has been the application of a negative pressure vacuum in a space between the limb (or a liner donned on the limb) and a socket or receptacle coupled to the prosthetic limb. Two conventional ways to apply such a vacuum are by a mechanical pump or an electronic pump.

Mechanical pumps are often in-line systems that utilize the movement of the user to generate the negative pressure vacuum in the socket. For example, the force generated by contacting the ground during a user's walking motion can be used to generate a vacuum in the socket space to hold the prosthesis to the user's limb. However, in utilizing the motion of the user, known pumps rely on complete compression of the pump to expel air from the pump before the pump can be decompressed to generate the vacuum. Because the impact and displacement of the pump is not consistent and varies between users, the vacuum and thus attachment between residual limb and the socket can be unpredictable and/or inadequate, causing the user discomfort, grief and even injury.

Yet another drawback is that many known pumps are integrated into the prosthetic limb in such a way that any failure of the pump would greatly impair the user's ability to walk. Many of such pumps are also bulky and significantly contribute to the weight of the prosthetic limb, imposing a significant weight burden on the user when walking.

There is a need for a vacuum suspension system that provides freedom of vacuum suspension for a prosthetic system. There is also a call for a vacuum suspension system that provides a secure vacuum without losing suction and confidence to the user over a period of user. It is also desirable for vacuum suspension systems to draw a vacuum while being lightweight and streamlined.

SUMMARY

Embodiments of the vacuum suspension system provide vacuum assisted suspension by generating negative pressure inside a prosthetic socket worn over a residual limb, and reducing sliding movement between the liner and the socket. The function of the embodiments is automatic as it is activated during gait. The weight placed on a prosthetic device of the system expands a pump mechanism that efficiently draws air out from the socket in each step, and expels it into the atmosphere during swing phase as the pump mechanism returns to an original configuration. The prosthetic device can be the socket, a prosthetic pylon, a prosthetic foot, an adaptor system, a prosthetic knee, or any other suitable device.

The pump mechanism utilizes the user's loading on the prosthetic device to create negative pressure into the socket without substantially affecting the functionality of the prosthetic device. It also does so without the use of complicated and bulky components as in the prior art, resulting in more secure and reliable elevated vacuum suspension. Furthermore, the pump mechanism can be a separate add-on module to the prosthetic system and can be adapted to fit a number of different prosthetic devices, providing versatility.

According to an embodiment, the vacuum suspension system includes a pump system arranged to be in fluid communication with a prosthetic socket. The pump system includes a pump mechanism having a housing and a membrane situated on the housing such that a fluid chamber is defined between the membrane and the housing. The pump mechanism is movable between an original configuration in which the volume of the fluid chamber is zero or near-zero, and an expanded configuration in which the volume of the fluid chamber is increased.

According to a variation, the pump system comprises a prosthetic adaptor adapted to form at least part of a load bearing connection between a prosthetic foot and the prosthetic socket. The pump system can include upper and lower sections arranged to move in an axial direction relative to one another, and the pump mechanism operatively connected to and positioned between the upper and lower sections such that when the pump system is loaded in stance the pump mechanism moves from the original configuration toward the expanded configuration.

During weight bearing (e.g., in stance phase), the upper section and the lower section move toward one another, which, in turn, moves the pump mechanism toward the expanded configuration and increases the volume of the fluid chamber. This increase in the volume of the fluid chamber creates a vacuum in the pump mechanism, pulling fluid into the pump mechanism from the socket. Weight bearing on the prosthetic connector thus automatically creates a vacuum in the pump mechanism.

After weight bearing (e.g., in swing phase), the pump mechanism returns toward the original configuration as the upper and lower sections move away from one another, expelling fluid within the fluid chamber. The pump mechanism can thus generate a vacuum in the socket during stance without undesirably affecting the functionality of the prosthetic foot or significantly increasing the bulk of the prosthetic device. In addition, the pump mechanism 126 can advantageously provide a dampening or shock absorbing effect to the prosthetic device, allowing for a more comfortable gait cycle.

According to a variation, the pump mechanism can be located at or near the socket such that there is no need to move fluid drawn into the pump mechanism from the socket down to the prosthetic foot. This advantageously reduces the time required to produce an elevated vacuum in the socket. Further, it eliminates or reduces the need of a long tube extending between the pump mechanism and the socket, reducing the likelihood of leaks and volume to generate vacuum. The pump mechanism embodiments can also be formed to be used with both left and right prosthetic feet or may be foot specific.

According to a variation, the pump system can include a biasing mechanism arranged to bias the pump mechanism toward the original configuration. When the pump system is loaded, the biasing mechanism can compress between the upper and lower sections. When the pump system is unloaded, the biasing mechanism decompresses and stored energy in the biasing mechanism drives the pump mechanism toward the original configuration.

BRIEF DESCRIPTION OF THE DRAWINGS

These and other features, aspects, and advantages of the present disclosure will become better understood regarding the following description, appended claims, and accompanying drawings.

FIG. 9 shows a side isometric view of a vacuum suspension system according to another embodiment.

FIG. 10 shows a side isometric view of the pump system in FIG. 9.

FIG. 11 shows a cross section view of the pump system in FIG. 9.

FIG. 12 shows another cross section view of the pump system in FIG. 9.

DETAILED DESCRIPTION OF THE DISCLOSURE

Figure 1:
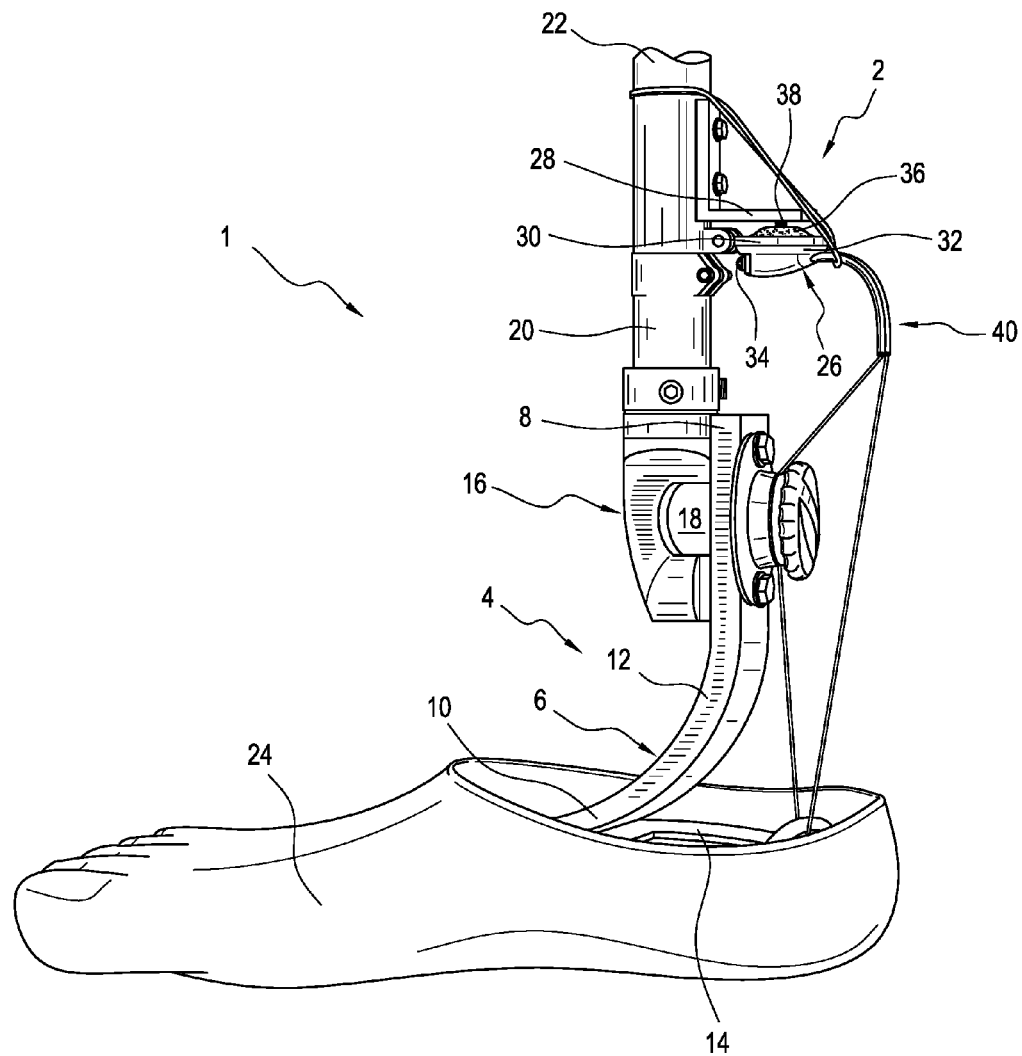
FIG. 1 shows a side view of a vacuum suspension system according to an embodiment.

It will be understood that, unless a term is expressly defined in this disclosure to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

The embodiments of one or more components of a vacuum suspension system will be described. A pump system having a fluid connection with a socket assists in creating a vacuum between a residual limb and the socket by pumping fluid out of the socket. The fluid can be pumped out of the socket when the user puts his weight on a prosthetic device (e.g., a prosthetic foot, a pylon, or prosthetic knee). The user's load on the prosthetic device can cause a pump mechanism of the pump system to increase the volume of a fluid chamber in the pump mechanism. The increase in volume of the pump mechanism draws in fluid from the vacuum space between the residual limb and the socket of a prosthetic limb. In this manner, the pump mechanism decreases the air pressure within the vacuum space causing a vacuum effect.

After the load is removed, and/or shifted on the prosthetic device, the volume of the fluid chamber in the pump mechanism is automatically decreased. The connection between the vacuum space and the pump mechanism may have a one-way valve assembly, so all of the air within the volume of the pump mechanism is expelled out of an outlet to another space or to atmosphere. The outlet is provided with a one-way valve assembly so the vacuum space is the only source of air.

The vacuum suspension system of the present disclosure produces a vacuum effect in a prosthetic socket that is advantageous over prior art devices that require compression of the pump to expel air before the pump can be decompressed to draw in air. The present disclosure also achieves smaller fluctuations in air pressure than the prior art systems, so the difference between the greatest pressure and lowest pressure in the vacuum space of the socket is less.

The pump mechanism embodiments may easily retrofit on existing prosthetic devices and can do so without undesirably affecting their function. They are also lightweight and low-profile, advantageously contributing little to no bulk to a prosthetic foot. Optionally, the pump mechanism embodiments can be located at or near the socket such that there is no need to move fluid drawn into the pump mechanism from the socket down to the prosthetic foot. This advantageously reduces the time required to produce an elevated vacuum in the socket. Further, it eliminates or reduces the need of a long tube extending between the prosthetic foot and the socket, reducing the likelihood of leaks and volume to generate vacuum. The pump mechanism embodiments can also be formed to be used with both left and right prosthetic feet or may be foot specific.

The efficiency of the pump mechanism is determined at least in part by how effectively the volume of the fluid chamber is reduced. Since the pump mechanism begins at and returns to the original state of zero or near-zero volume at the beginning or end of each cycle in some embodiments, the volume of the fluid chamber is determined by the force applied to the pump, not by a full compression and recompression cycle as in the prior art. In addition, all fluid drawn into the pump mechanism is expelled afterwards, fully utilizing the volume of the fluid chamber.

The vacuum suspension system also reduces volume fluctuations of the residual limb and allows for increased proprioception and reduced pistoning since there is a better attachment between the socket and the residual limb. It may also be beneficial to produce hypobaric pressure below a certain level in the socket. This may be achieved using a sealing membrane or seal component between the residual limb and the socket, instead of the conventional sealing method of using a sleeve to form an airtight connection between the residual limb and the proximal end of the socket. The sealing membrane may be on a prosthetic liner as described in U.S. Pat. No. 8,034,120 incorporated by reference and belonging to the assignee of this disclosure.

The benefit of using a liner having a seal or seal component reduces the volume of air to be drawn out of the socket and therefore, a better suspension may be achieved in a shorter time period. Using a silicone liner with integrated seal also provides the added benefit that the hypobaric region is not directly applied to the skin.

The vacuum pump mechanisms in the embodiments of the prosthetic device described are generally described as a pump system or mechanism and may include any suitable type of pump mechanism. For instance, the pump mechanism may be a pump as described in U.S. provisional application 62/019,674 incorporated by reference and belonging to the assignee of this disclosure. A piston-type pump may be used in the embodiments in place of a membrane-type pump. A bladder-type pump may also be used in the embodiments in place of a membrane-type pump, and a skilled person would understand that the pump mechanisms described may also be used with a bladder-type pump and vice versa.

A bladder-type pump has an interior fluid chamber surrounded by an airtight material. When the interior chamber is expanded, the opposing walls are moved away from each other by extending at least one side wall of the pump. The side walls of the bladder-type pump may have an accordion-like shape or be formed of a polymeric material which allow for the increase in distance between the opposing walls.

A membrane-type pump has at least one wall of flexible material and a second opposing wall which may be rigid or flexible. The edges of the two walls are attached to each other such that when a force applies to the pump to expand the interior fluid chamber, the force deforms at least the flexible wall, and the flexible wall arcs outward to form an interior fluid chamber. To allow for deformation, the flexible wall may be made of a polymeric material including elastomeric material such as rubber or plastic.

The bladder-type pump and membrane-type pump are arranged so that when no force applies to the pump or no weight is placed on the prosthetic device the volume of the interior fluid chamber is zero or near-zero. The pumps described and shown have a cylindrical shape. A skilled person would understand that the pumps may have a variety of shapes, for example, a diamond, rectangular, or triangular shape.

The specific embodiments of the prosthetic device will now be described regarding the figures.

Figure 2:
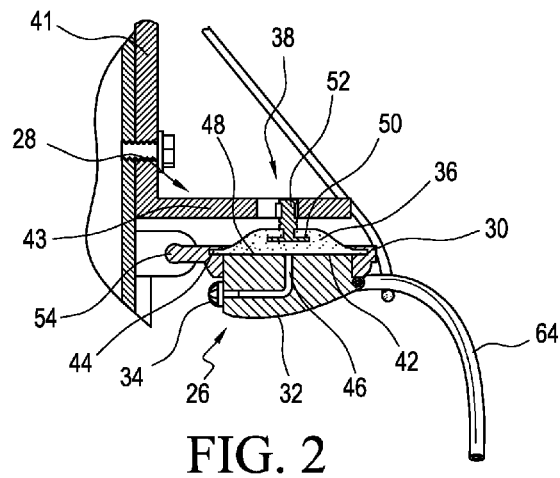
FIG. 2 shows a detailed side view of the pump system in FIG. 1.

FIGS. 1 and 2 show a vacuum suspension system 1 comprising a pump system 2 and a prosthetic foot 4 according to an embodiment. As seen in FIG. 1, the prosthetic foot 4 can be any suitable prosthetic foot but is shown having a foot member 6 that extends from a proximal section 8 terminating at a proximal end to a distal section 10 terminating at a distal end. The proximal section 8 can be generally vertically oriented, and the distal section 10 can be generally horizontally oriented.

The foot member 6 can have a curved portion 12 between the proximal section 8 and the distal section 10 that is generally forwardly-facing concave. The curved portion 12 and/or the proximal section 8 can be generally at a location of a natural human ankle. The prosthetic foot 4 can have a heel member 14 that extends rearwardly from the foot member 6 and is disposed below at least a portion of the foot member 6. The heel member 14 can have a curvilinear profile along its length.

An adaptor 16 can be coupled to the anterior surface of the proximal section 8 of the foot member 6. Advantageously, the adaptor 16 can have a hole 18 or a hollowed-out portion to reduce the weight of the adaptor 16. An adhesive or bonding agent (e.g., epoxy) can be applied to the proximal section 8 or the posterior surface of the adaptor 16 to secure the adaptor 16 to the proximal section 8 of the foot member 6. Alternatively, fasteners or other hardware can be used to secure the adaptor 16 to the foot member 6.

A connector 20 can be disposed on the proximal end of the adaptor 16 for coupling the foot member 6 to a prosthetic pylon 22 or socket. The connector 20 can be a male pyramid connector, a tube clamp, or other attachment device. The connector can be secured to the adaptor 16 with adhesive or bonding agent. The connector 20 can also be secured to the adaptor 16 with fasteners or other hardware. Additionally, or alternatively, the connector 20 can be threadedly attached to the adaptor 16.

In use, the prosthetic foot 4 can expand and compress. The prosthetic foot 4 is in expansion when the proximal end of the foot member 6 and the heel member 14 are moved together from a resting position of the foot, reducing the distance between the foot member and the heel member. The prosthetic foot 4 is in compression when the proximal end of the foot member 6 and the heel member 14 are moved apart from the resting position of the foot, increasing the distance between the foot member and heel member 14.

Additional prosthetic foot designs that can include the pump system embodiments disclosed herein can include, but are not limited to, the following models by Össur of Rekjavik, Iceland: Axia™, Ceterus™, Elation™, LP Ceterus™, LP Vari-Flex™, Modular III™, Re-Flex VSP®, Cheetah™, Flex-Sprint™, Flex-Run™, Talux™, Vari-Flex™, Flex-Foot® Junior, Sure-Flex, Vari-Flex XC Rotate™, LP Rotate™, LP Re-Flex VSP, Re-flex Rotate™, Re-Flex Shock™, Flex-Foot Balance, Flex-Foot Assure, and Balance™ Foot J. This disclosure is incorporated by reference and belongs to the assignee of this disclosure.

Optionally, the prosthetic foot 4 may be insertable into a foot cover 24 as seen in FIG. 1. The bottom surface of the foot member 6 and/or a rear surface of the heel member 14 can be shaped to generally correspond to the curvature and shape of the inner surfaces of a foot cover.

In order to better understand the operation of the prosthetic foot 4, a basic discussion of the gait cycle is required. The gait cycle defines the movement of the leg between successive heel contacts of the same foot. The gait cycle has two phases: stance and swing. Of particular interest is the stance phase which generally includes heel-strike or initial contact, mid-stance, and toe-off.

It is during the stance phase that the mechanics of a prosthetic foot 4 come into play. Upon heel strike, the prosthetic foot 4 is in expansion, providing cushioning to the user. During mid-stance, at which time the weight of the user is transmitted through the prosthetic foot 4 to a supporting surface, the prosthetic foot 4 moves from expansion into compression. The prosthetic foot 4 remains in compression through toe-off until the weight of the user is removed from the prosthetic foot, at which time the prosthetic foot 4 returns to its resting position.

The pump system 2 can be coupled to the prosthetic device at any suitable location but is shown coupled between the heel member 14 and the pylon 22. The pump system 2 can be formed to be used with both left and right prosthetic feet. Alternatively, the pump system 2 can be formed to be used specifically on a left or right prosthetic foot.

The pump system 2 can include a pump mechanism 26 made generally from carbon fiber and/or plastic, and an elastomeric compound (e.g., a membrane) providing durable yet lightweight components. Prior art pump mechanisms are of heavy metal construction, which imposes a significant weight burden on the user when walking.

The pump mechanism can be secured to the pylon 22. For instance, the pump mechanism 26 can be located between a support member 28 extending rearwardly from the pylon 22 and a movable member 30 connected to the pylon 22 below the support member 28. Because the pump mechanism is secured to the pylon 22, it advantageously does not add volume to the prosthetic foot 4 and/or foot cover 24.

The pump mechanism 26 includes a housing 32 containing one or more valve assemblies 34, a membrane 36, a connector 38, and a connecting system 40. The one or more valve assemblies 34 can include a one-way valve, also referred to as a check valve. A preferred type of one-way valve used is a duckbill valve. It should be appreciated however that other types of one-way valves are possible.

The one or more valve assemblies 34 can include an inlet valve assembly arranged to only allow fluid to enter the pump mechanism 26 and can optionally be connected to a tube. The pump mechanism 26 can be in fluid communication with the cavity of a prosthetic socket. When the volume of the pump mechanism 26 increases, fluid (e.g., air) can be drawn out from the socket via the inlet valve assembly. The at least one valve assembly 34 can include an outlet valve assembly arranged to only allow fluid to be expelled out of the pump mechanism 26, preferably to atmosphere. The outlet valve assembly may include a silencer.

Because the pump mechanism 26 is located away from the foot 4 and toward the socket, there is no need to move the fluid drawn into the pump mechanism from the socket down to the prosthetic foot, advantageously reducing the time required to produce an elevated vacuum in the socket. Further, it eliminates the need of a long tube extending between the prosthetic foot and the socket and the likelihood of leaks in the pump system 2.

Referring to FIG. 2, the top surface of the housing 32 defines a cavity 42 that is provided with an undercut circumferential groove 44 between an open end of the cavity 42 and a closed bottom of the cavity. An outer radial edge of the membrane 36 can be situated in the circumferential groove 44 such that a seal is formed between the membrane 36 and the housing 32. Optionally, an adhesive can be applied between the housing 32 and the outer radial edge of the membrane 36, increasing the sealing effect. The bottom of the cavity has one or more openings 46 which extend into the housing 32 to form internal passageways providing fluid communication between a fluid chamber 48 defined between the bottom of the cavity and a bottom surface of the membrane 36, and the at least one valve assembly 34.

The pump mechanism 36 relies upon deformation of the membrane 36 to move between an original configuration (shown in FIG. 2) in which the volume of the fluid chamber 48 is zero or near-zero, and an expanded configuration (shown in FIG. 3) in which the volume of the fluid chamber 48 is increased.

When a force F is exerted on the membrane 36 in a direction away from the housing 32, the pump mechanism 26 moves toward the expanded configuration (shown in FIG. 3) as the force F pulls the bottom of the cavity away from a portion of the membrane 26, causing deformation of the membrane 36 and an increase in volume of the fluid chamber 48. This increase in volume of the fluid chamber 48 can draw fluid into the fluid chamber from the socket through the one or more valve assemblies 34. The housing 32 may be formed of metal such as stainless steel, carbon fiber, or plastic or any other material which would provide sufficient strength to resist deformation when pulled away from the membrane 36.

Once the force is removed from the membrane 36, the pump mechanism 26 returns toward its original configuration (shown in FIG. 2) as the membrane 36 returns toward the bottom of the cavity and fluid within the fluid chamber 48 is expelled out of the one or more valve assemblies 34. The membrane 36 can be elastomeric and can use at least in part its material properties to naturally or elastically return to its original position on the bottom of the cavity.

The membrane 36 may have any desired shape, but is shown having a generally circular or elliptical shape. The membrane 36 can be operatively attached at or near its center point to the support member 28 while the outer radial edge portion of the membrane 36 is attached to the housing 32 such that when the housing 32 is pulled away from the membrane 36 a pocket forms in a middle area of the membrane 36 due to the deformation of the membrane 36. The formation of the pocket increases the volume of the fluid chamber 48. The pump mechanism 26 thus uses a compliant membrane to create suction.

As seen in FIG. 2, the connector 38 can be an insert having a lower radial flange 50 embedded in the membrane 36 and a shaft portion 52 extending between the lower flange 50 and support member 28. In some embodiments, the connector 38 may be of a two-piece construction such that the shaft portion 52 can be threadedly removed from the lower flange embedded in the membrane 36. The connector 38 may be formed of metal, plastic, or any suitable other material. In other embodiments, the lower flange may extend substantially into the membrane 36 or may be formed of a material that is part of the membrane 36 (e.g. a flexible metal member).

Other examples of the pump mechanism are described in U.S. patent application Ser. Nos. 13/873,394; 13/873,315; 13/766,086; 62/101,154; and 62/151,518, and commercially available as the Unity Vacuum System by Össur hf. This disclosure is incorporated by reference and belongs to the assignee of this disclosure.

The support member 28 can include a generally upright section 42 attached to the pylon 22 and a generally horizontal section 44 extending rearwardly from the section 42 and connected to the membrane 36 via the connector 38. The sections 42, 44 can extend at any suitable angle relative to the pylon 22.

The support member 28 can define an opening or slot for receiving the connector 38. To attach the support member 28 to the membrane 36, the shaft portion of the connector 38 can be received in the opening or slot such that the section 44 of the support member 28 is connected to the connector 38. The connector 38 can be threadedly attached to the support member 28. The connector 38 can be attached to the support 38 via a pin, nut, or other fastener. Through the structure of the connector 38 and the support member 28, the pump mechanism 26 has the benefit of being easily and quickly removed and/or replaced from the prosthetic foot 4.

The movable member 30 can be secured to the pylon 22 at a location below the support member 28 and movable relative to the support member 28. The movable member 30 can be a plate pivotally connected to the pylon 22 at a pivot point 54. In other embodiments, the movable member 30 can be a plate arranged to flexibly rotate relative to the support member 38.

The membrane 36 can rest within an opening 56 defined in the movable member 30. The housing 32 can have a portion which extends beyond the membrane 36 to engage the bottom surface of the movable member 30 surrounding the opening 56 and allows the movable member 30 to pull the housing 32 away from the membrane 36 when flexed.

Figure 3:
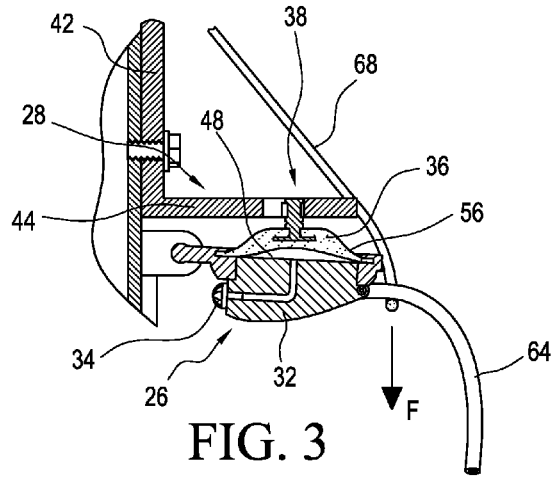
FIG. 3 shows another detailed side view of the pump system in FIG. 1.
Figure 4:
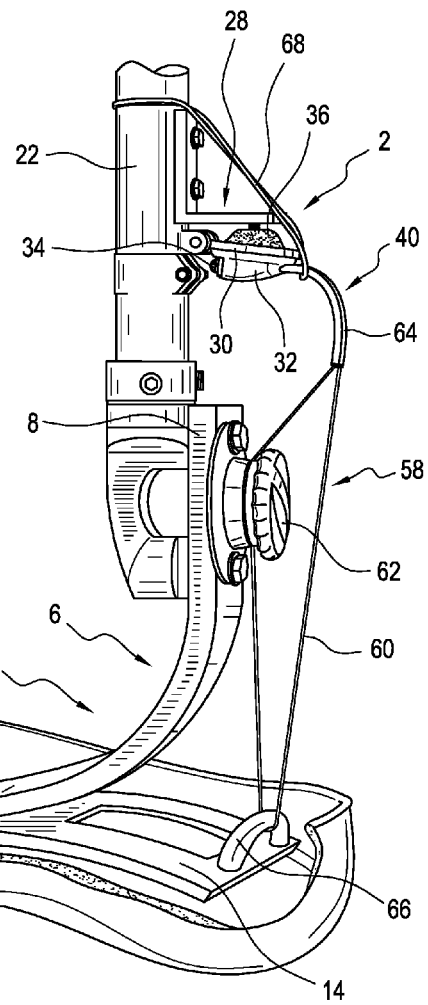
FIG. 4 shows partial cutaway view of the vacuum suspension system in FIG. 1.

Referring to FIGS. 3 and 4, a tensioning system 58 operatively connects the pump mechanism 26 to the prosthetic foot 4. The tensioning system 58 can include a tensioning element 60 that is secured to and adjusted by a tensioning control mechanism 62 to adjust the length of the tensioning element 60. The tensioning element 60 can be a cable, a lace, wire or any other suitable member and may refer to a relatively long and relatively thin shaped metals or polymers, which may be single strand or multi-strand, and which may include friction reducing coatings thereon. The tensioning element 60 translates action of the prosthetic foot 4 to the pump mechanism 26.

The tensioning control mechanism 62 can be a dial-tensioning control mechanism arranged for incremental and preselected adjustment in the tension of the tensioning element 60. The tensioning control mechanism 62 is not limited to the example provided above but can include any system that permits adjusting tension in the tensioning element 60. The tensioning control mechanism 62 also allows the tensioning element 60 to be fixed at a desired length.

The dial-tensioning control mechanism 62 can be secured to the posterior surface of the proximal section 8 of the foot member 6, with the tensioning element 60 extending from both the proximal and distal sides of the dial-tensioning control mechanism 62. It should be noted that the ends of the tensioning element 60 can be retained within the dial-tensioning control mechanism 62 and the portion of the tensioning element 60 outside the dial-tensioning control mechanism 62 extends continuously between the connecting system 40, the heel member 14, and the dial-tensioning control mechanism 62 without interruption.

As seen, the connecting system 40 of the pump system 2 can include at least one arm member 64 attached to the housing 32. The arm member 64 can include a first portion extending rearwardly from the housing 32 and a second portion curving downwardly toward the heel member 14.

A first end of the tensioning element 60 is attached to the dial-tensioning control mechanism 62. From the dial-tensioning control mechanism 62, the tensioning element 60 extends through the connecting system 40. From the connecting system 40, the tensioning element 60 extends downwardly toward the heel member 14. The tensioning element 60 then passes an anchor point 66 on the heel member 14 which in turn directs the tensioning element 60 back toward the dial-tensioning control mechanism 62. At the dial-tensioning control mechanism 62, a second end of the tensioning element 60 is attached to the dial-tensioning control mechanism 62.

Because only the tensioning element 60 is attached to the prosthetic foot 4, the likelihood of the pump system 2 undesirably affecting the prosthetic foot 4 is advantageously reduced.

When the prosthetic foot 4 is in the resting position (shown in FIG. 1), the pump mechanism 26 is in its original configuration. Upon heel strike, the prosthetic foot 4 moves into expansion, which, in turn, creates slack in the tensioning element 60. With the prosthetic foot 4 in expansion, the pump mechanism 26 remains in its original configuration.

As the prosthetic foot 4 moves from heel strike through mid-stance and/or toe-off, the prosthetic foot 4 moves into compression. In compression, the proximal end of the foot member 6 moves away from the heel member 14 causing the tensioning element 60 to tighten and apply a downward or pulling force on the connecting system 40 of the pump system 2 as shown in FIG. 4.

The downward force on the connecting system 40 causes the housing 32 and the movable member 30 to pivot and/or flex away from the support member 28. This moves the housing 32 away from the membrane 36, moving the pump mechanism 26 to the expanded configuration. More particularly, the support member 28 pulls the housing 32 away from the membrane 36, increasing the volume of the fluid chamber 48. Optionally, a spring member may be serially connected to the tensioning element 60 which allows for movement without changing the stiffness of the prosthetic foot 4 too much. Further, the spring member can also reduce the likelihood of the tensioning element 60 pulling too hard on the pump mechanism 26.

This increase in volume of the fluid chamber 48 creates a vacuum in the pump mechanism 26, pulling fluid into the pump mechanism 26 through the one or more valve assemblies 34. Compression of the prosthetic foot thus automatically creates a vacuum in the pump mechanism 26. This is advantageous over prior art prosthetic devices that require compression of the pump to expel air before the pump can be decompressed to draw in air. Further, because the pump mechanism 26 does not need to be first compressed before it can create a vacuum upon decompression, the pump mechanism 26 can achieve smaller fluctuations in air pressure than the prior art devices, so the difference between the greatest pressure and lowest pressure in the vacuum space of the socket is less than compared to the prior art devices.

At the end of the stance phase or when the weight of the user is removed from the prosthetic foot 4, the prosthetic foot 4 returns to its resting position and a biasing mechanism 68 extending between the pylon 22 and the connecting system 40 can help return the movable member 30 to its resting position, moving the pump mechanism 26 back toward its original configuration and decreasing the volume of the fluid chamber to a zero or near zero volume.

During the return of the membrane 36 toward the housing 32, the pump mechanism 26 expels fluid in the fluid chamber 48 out of the one or more valve assemblies 34. Because of the pump mechanism 26 returns to its original configuration of zero or near-zero volume in the fluid chamber at the beginning or end of each gait cycle, substantially all fluid drawn into the pump mechanism 26 is automatically expelled. This is advantageous because prior art devices rely on complete compression of the pump in expelling air in each gait cycle to use the pump to its maximum capacity. It is difficult for complete compression to occur in every cycle using the gait of a user as the actuating force since the impact and displacement of the pump is not consistent and varies between users.

The dial-tensioning control mechanism 62 may be rotated in a first direction to decrease the length of the tensioning element 60 and thereby increase the tension in the tensioning element 60. To increase the length of the tensioning element 60 and thereby decrease the tension in the tensioning element 60, the dial-tensioning control mechanism 62 may be rotated in a second direction.

By adjusting the tension in the tensioning element 60, the sensitivity of the pump mechanism 26 can be varied. For instance, by increasing the tension in the tensioning element 60, the level of pre-load applied to the housing 32 may be increased, increasing the sensitivity of the pump mechanism 26 to the action of the prosthetic foot 4, It will be appreciated that the sensitivity of the pump mechanism 26 may be varied based on user activity level, weight, and/or other factors, advantageously providing greater control and versatility.

FIGS. 5-8 show a prosthetic device or a vacuum suspension system 70 including a pump system 72 according to another embodiment. The vacuum suspension system 70 has a socket 76, a liner 78 preferably including a seal component, and a prosthetic foot 74. The socket 76 defines an interior space, and an interior wall delimiting the interior shape. The vacuum suspension system 70 includes an adapter system 80 for coupling the socket 76 to a prosthetic pylon, prosthetic foot, a rotation module, a shock module, or other suitable component.

The vacuum suspension system 70 provides improved proprioception and volume control. The vacuum suspension system 70 includes a pump mechanism 82, as discussed in earlier embodiments, which provides a vacuum assisted suspension by generating a negative pressure (vacuum) inside the socket 76. As seen, the pump mechanism 82 can be attached directly to the socket 76.

An actuator comprising a cable member 104 extends between the pump mechanism 82 and a heel member of the prosthetic foot 74. Because the pump mechanism 82 is located on the socket 76, fluid drawn into the pump mechanism 82 from the socket 76 does not have to be drawn down to the prosthetic foot 74, advantageously increasing efficiency and reducing the time required to produce an elevated vacuum in the socket 76.

Figure 6:
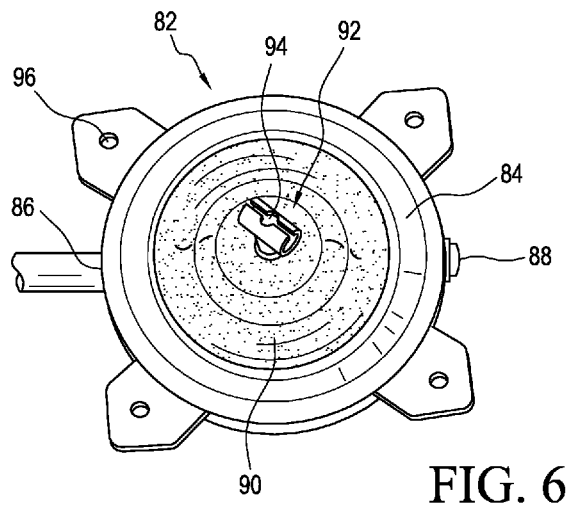
FIG. 6 shows a front view of the pump system in FIG. 5.
Figure 7:
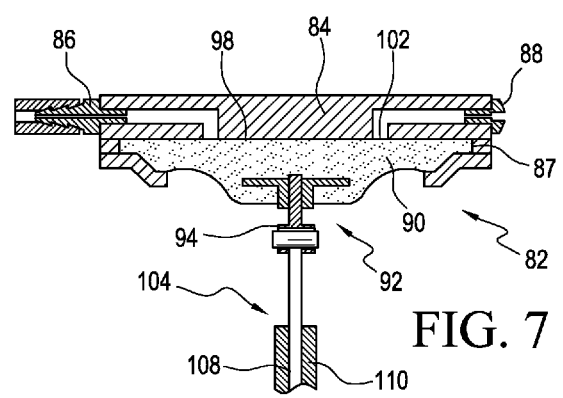
FIG. 7 shows a cross section view of the pump system in FIG. 5.
Figure 8:
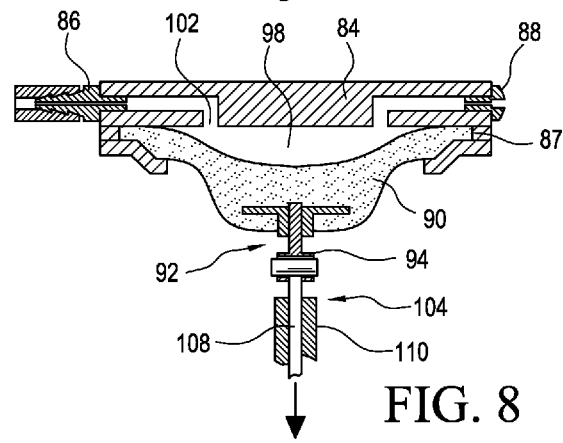
FIG. 8 shows another cross section view of the pump system in FIG. 5.

Referring to FIGS. 6-8, the pump mechanism 82 includes a housing 84 containing two one-way valve assemblies 86, 88, a membrane 90, and a connector 92. The valve assembly 86 is arranged to only allow fluid to enter the pump mechanism 82, which can be in fluid communication with the cavity of the socket 76. The valve assembly 88 is arranged to only allow fluid to be expelled out of the pump mechanism 82, preferably to atmosphere. The connector 92 is connected to the membrane 90 and includes an attachment portion 94 above the membrane 90, and a shaft portion extending from the membrane 90 to the attachment portion. The housing 84 can include at least one fastener hole 96 arranged to receive at least one fastener for attaching the pump mechanism 82 to the socket 76.

FIGS. 7 and 8 show cross section views of the pump mechanism 82. Similar to the pump mechanism 26, the pump mechanism 82 relies upon deformation of the membrane 90 to move between an original configuration (shown in FIG. 7) in which the volume of a fluid chamber 98 defined between the top surface of the membrane 90 and the bottom of the housing 84 is zero or near-zero, and an expanded configuration (shown in FIG. 8) in which the volume of the fluid chamber 98 is increased. The membrane 90 can be positioned in a cavity of the housing 84. The housing 84 surrounds the outer radial edge portion of the membrane 90 and creates a seal with the membrane 90. For instance, the cavity is provided with an undercut circumferential groove 87 within which the outer radial edge of the membrane 90 is situated.

The bottom surface of the cavity defines a pair of openings 102 which extend into the housing 84 to form internal passageways to provide fluid communication between the fluid chamber 98 and the two one-way valve assemblies 86, 88.

Figure 5:
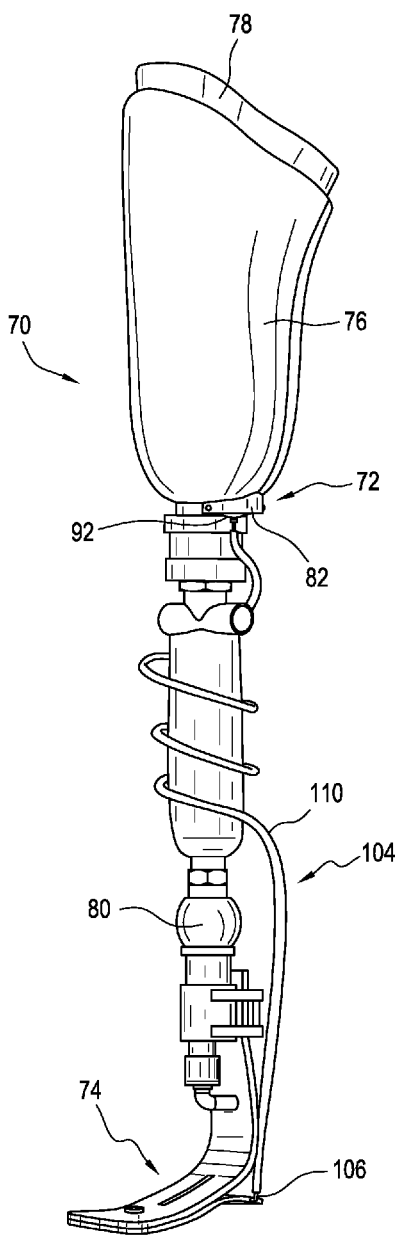
FIG. 5 shows a side isometric view of a vacuum suspension system according to an embodiment.

As seen in FIG. 5, the cable 104 is connected at a first end to the connector 92 and at a second end to anchor point 106 on the prosthetic foot 74. Because only the cable 104 is attached to the prosthetic foot 74, the likelihood of the pump system 82 undesirably impeding action of the prosthetic foot 74 is advantageously reduced. Further, the pump system 82 does not add additional volume to the prosthetic foot 74 and/or a foot cover.

Referring to FIGS. 7 and 8, the cable 104 can include a core 108 slidably positioned within a tubular casing or sheath 110. The sheath 110 is arranged to provide axial stiffness to the core 108 such that a force on the second end of the cable 104 forces the core 108 upward or downward relative to the sheath 110, moving the pump mechanism 82 between the original configuration and the expanded configuration. Optionally, the cable 104 can be wrapped around the adaptor system 80 and/or another component extending between the socket 76 and the adaptor system 80.

The function of the vacuum suspension system 70 can be fully automatic. During mid-stance and/or toe-off, compression of the prosthetic foot 74 causes the cable 104 to pull the membrane 90 away from the housing 84, which, in turn, expands the pump mechanism 82 to efficiently draw fluid out of the socket 76. During the swing phase, decompression of the prosthetic foot 74 permits the pump mechanism 82 to return to its original position, expelling the fluid drawn from the socket 76 to atmosphere. The pump mechanism 82 thus can create a negative pressure inside the socket 76, resulting in a secure and reliable elevated vacuum suspension that provides an intimate suspension as the negative pressure formed inside of the socket 76 holds the liner and the residuum firmly to the socket wall.

FIGS. 9-12 show a prosthetic device or a vacuum suspension system 110 including a pump system 112 according to another embodiment. The vacuum suspension system 110 has a socket 114, a valve 116, and a tube 118 connecting a pump mechanism 126 of the pump system 112 to the socket 114, and a prosthetic foot 120. The vacuum suspension system 110 includes an adaptor system 124 for coupling the socket 114 to a prosthetic pylon 122 attached to the prosthetic foot 120.

The vacuum suspension system 110 includes the pump system 112, as discussed in earlier embodiments, which provides a vacuum suspension by generating a vacuum inside the socket 114. As seen, the pump system 112 can comprise a prosthetic connector adapted to form at least part of a load bearing connection between the foot 120 and the socket 114. For instance, the prosthetic connector can connect the socket 114 to the pylon 122, which is attached to the foot 120. As such, the pump system 112 can help support loads exerted on the socket 114 and transfer such loads to the ground or other underlying surface via the pylon 122 and the foot 120. The pump system 112 can easily retrofit on existing prosthetic devices and can be formed for right and left prosthetic devices. For instance, the pump system 112 can easily retrofit on an existing prosthetic device by selecting a pylon compatible with the pump system 112. The pump system 112 can be substantially in axial alignment with the pylon 122.

Because the pump mechanism 126 of the pump system 112 can be located at or near the socket 114, fluid drawn from the socket 114 by the pump mechanism 126 does not have to be moved down to the foot 122. This has the effect of reducing the time required to generate an elevated vacuum in the socket 114. This also reduces the length of the tube 118, reducing the likelihood of leaks in the pump system 112. It further helps reduce the overall volume of the pump system 112. In other embodiments, the pump mechanism 126 can be integrated into the attachment between the prosthetic foot 120 and another component. In other embodiments, the pump mechanism 126 can be integrated into a prosthetic pylon 122.

Referring to FIGS. 10-12, the pump system 112 includes an upper section 130, a lower section 132, and a pump mechanism 126. The upper section 130 and the lower section 132 are arranged to move in an axial direction relative to one another. The upper section 130 can define an adaptor 134 having a female configuration arranged to receive a male adaptor, a tube, or other component. The lower section 132 can define an adaptor 136 having a similar configuration. In other embodiments, the adaptors 134, 136 can be male adaptors or other type of connectors.

The upper section 130 defines a cavity 138 having a peripheral internal cavity wall 140 extending between a bottom opening 142 at or near the bottom of the upper section 130 and a closed end 144 (shown in FIG. 11). The cavity 138 is shown having a generally cylindrical shape but can have any suitable shape. A pin member 146 protrudes downward from the upper wall 144 of the cavity 138. The pin member 146 can have a hollow configuration defining an internal channel extending through the pin member 146.

The upper section 130 includes valve assemblies 160, 162. The valve assembly 160 is arranged to only allow fluid to enter the pump mechanism 126 and can be connected to the tube 118. The valve assembly 162 is arranged to only allow fluid to be expelled out of the pump mechanism 126, preferably to atmosphere. An internal passageway 152 is arranged to provide fluid communication between the valve assemblies 160, 162 and the pin member 146. Optionally, a lower end section of the pin member 146 can define one or more perforations providing fluid communication between the internal passageway 152 and a fluid chamber defined below.

The lower section 132 is sized and configured to fit into the cavity 138 of the upper section 130 via the bottom opening 142. The lower section 132 defines a cavity 154 to accommodate a membrane described below.

The pump mechanism 126 includes a housing 148 and a membrane 152. The housing 148 defines a through opening 150 arranged to allow the pin member 146 to slidably pass therethrough. The housing 148 can have a rigid configuration. The membrane 152 is positioned below the housing 148. The cavity 154 can be dimensioned to allow a center portion of the membrane 152 to move in a downward direction within the lower section 132 when the membrane 152 is pushed downward by the pin member 146 as described below.

An outer radial edge of the membrane 152 can be attached to the housing 148 such that a seal is formed between the membrane 152 and the housing 148. Optionally, an adhesive can be applied between the housing 148 and the outer radial edge of the membrane 152, increasing the sealing effect. The fluid passageway 152 can be in fluid communication with a fluid chamber 158 defined between the upper surface of the membrane 152 and the bottom of the housing 148.

Similar to the other embodiments, the pump mechanism 126 relies upon deformation of the membrane 152 to move between an original configuration (shown in FIG. 11) in which the volume of the fluid chamber 158 is zero or near-zero, and an expanded configuration (shown in FIG. 12) in which the volume of the fluid chamber 158 is increased.

During weight bearing (e.g., in stance phase), the pump mechanism 126 moves toward the expanded configuration (shown in FIG. 12). More particularly, the upper section 130 and the lower section 132 move toward one another, which, in turn, causes the pin member 146 to push the center portion of the membrane 152 away from the bottom of the housing 148, increasing the volume of the fluid chamber 158. This increase in volume of the fluid chamber 158 creates a vacuum in the pump mechanism 126, pulling fluid into the pump mechanism 126 through the inlet valve assembly 160. Weight bearing on the prosthetic connector thus automatically creates a vacuum in the pump mechanism 126.

After weight bearing (e.g., in swing phase), the pump mechanism 136 returns toward the original configuration (shown in FIG. 11) as the upper and lower sections 130, 132 move away from one another. This moves the pin member 146 away from the membrane 152, allowing the membrane 152 to return toward the bottom of the housing 148 and to expel fluid within the fluid chamber 158 out of the valve assembly 162. Optionally, the pin member 146 can be attached to the membrane 152 such that it can pull the membrane 152 back to its original position after weight bearing.

It will be appreciated that the membrane 152 can be elastomeric and can use at least in part its material properties to naturally or elastically return to the its original position on the bottom of the housing 148. The membrane 152 can have any desired shape. In other embodiments, the weight of the prosthesis or foot 120 below the pump mechanism 126 can help move the pump mechanism 126 toward the original configuration.

Optionally, the pump mechanism 126 can include a biasing mechanism 164 arranged to bias the pump mechanism 126 toward the original configuration. The biasing mechanism 164 can comprise a ring member having a compressible configuration situated in the cavity 138. The biasing mechanism 164 can be resilient such as an elastomeric material and/or any other material that deforms under a load and returns to its original form or position when the load is released. During weight bearing, the biasing mechanism 164 can compress between the housing 148 and the upper section 130. After weight bearing, the biasing mechanism 164 can decompress and stored energy in the biasing mechanism 164 can drive the pump mechanism 126 toward the original configuration.

The pump mechanism 126 can thus generate a vacuum in the socket 114 during stance without undesirably affecting the functionality of the prosthetic foot 120 or significantly increasing the bulk of the prosthetic device. In addition, the pump mechanism 126 can advantageously provide a dampening or shock absorbing effect to the prosthetic device, allowing for a more comfortable gait cycle.

According to a variation, at least one sensor can be incorporated into the pump system 112. For instance, the pump system 112 can include at least one sensor 129 including, but not limited to, one or more Hall Effect sensors, linear variable displacement transducers, differential variable reluctance transducers, or reed switches. The at least one sensor 129 can be incorporated in the upper section 130 and/or the lower section 132 and arranged to measure one or more relationships between the two components. For instance, the at least one sensor 129 can be used to measure force or positional changes between the upper and lower sections 130, 132. In an embodiment, a Hall Effect sensor can be used to monitor angular changes between the upper and lower sections 130, 132. The output from the at least one sensor 129 can be used to regulate pressure in the socket 114. In other embodiments, the output from the at least one sensor 129 can be used for general sensory feedback information on gait and performance characteristics.

Figure 13:
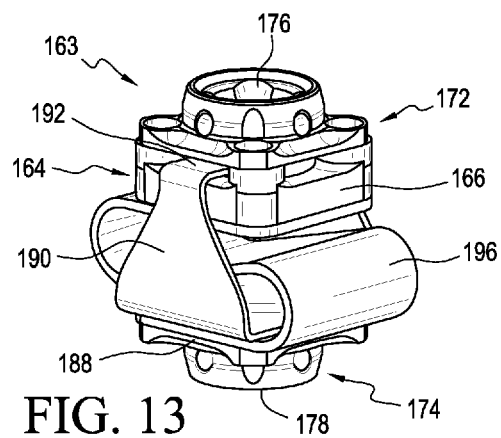
FIG. 13 shows a side isometric view of a pump system according to another embodiment.
Figure 14:
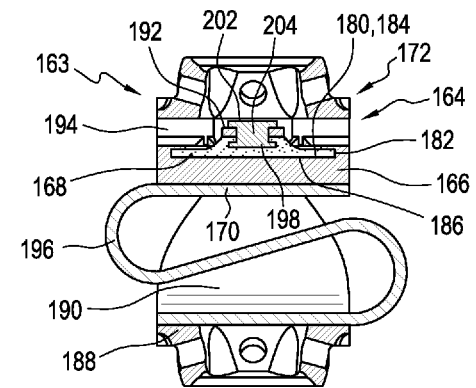
FIG. 14 shows a cross section view of the pump system in FIG. 13.
Figure 15:
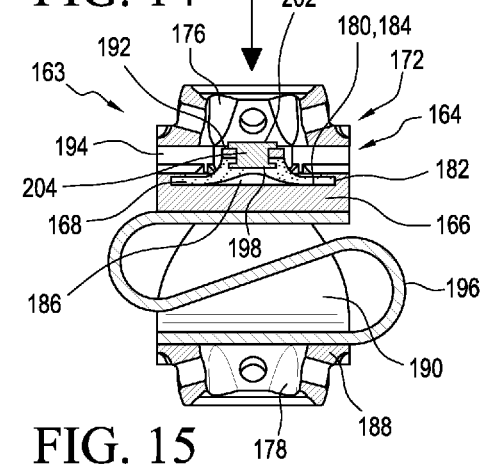
FIG. 15 shows another cross section view of the pump system in FIG. 13.

FIGS. 13-15 illustrate a pump system 163 according to another embodiment that can be integrated in the adaptor system of a prosthetic device. In the illustrated embodiment, the pump system 163 can comprise a prosthetic connector adapted to form a connection between a prosthetic foot and a socket. The pump system 163 can include a pump mechanism 164, an upper section 172, and a lower section 174. At least one of the upper and lower sections 172, 174 is movable axially relative to the other. The upper section 172 can include an adaptor 176 and the lower section 174 can include an adaptor 178. The adaptors 176, 178 are shown as female adaptors but can be male adaptors or other types of connectors.

The pump mechanism 164 includes a housing 166, a membrane 168, and a connector 170. It will be appreciated that the pump mechanism 164 may include one or more valve assemblies similar to the other embodiments arranged to control movement of fluid into and from the pump mechanism 126. Referring to FIG. 14, the housing 166 can be located in the upper section 172. The housing 166 defines a cavity 180 provided with an undercut circumferential groove 182 between an open end of the cavity 182 and a closed end 184 of the cavity 180. An outer radial edge portion of the membrane 168 can be situated in the circumferential groove 182 such that a seal is formed between the membrane 168 and the housing 166. The closed end 184 of the cavity 180 can define one or more openings which extend into the housing 166 to form internal passageways providing fluid communication between a fluid chamber defined below and one or more valve assemblies.

The pump mechanism 164 is movable between an original configuration (FIG. 14) in which the volume of a fluid chamber 186 defined between the bottom surface of the membrane 168 and the closed end 184 of the cavity 180 is zero or near-zero, and an expanded configuration (shown in FIG. 15) in which the volume of the fluid chamber 186 is increased. The bottom 184 of the cavity 180 substantially complements the bottom surface of the membrane 168 such that when no force is exerted on the pump mechanism 164 it is in the original position.

The lower section 174 includes a base 188 and arms 190 on each side of the base 188 that extend upwardly from the base 188. A cross member 192 is formed between the arms 190. The cross member 192 extends through an open space 194 formed of the upper section 174 over the housing 166. A resilient element 196 connects the upper section 172 to the lower section 174. The resilient element 196 can be a spring member. The spring member can have a folded structure.

The membrane 168 may have any desired shape, but is shown having a generally circular or elliptical shape. The membrane 168 can be operatively attached at or near its center point to the cross member 192 of the lower section 174 while the outer radial edge portion of the membrane 168 is attached to the upper section 172 such that when the membrane 168 is pulled away from the upper section 172 a pocket forms in a middle area of the membrane 168 due to the deformation of the membrane 168. The formation of the pocket increases the volume of the fluid chamber 186.

During weight bearing or when a load is applied to a socket or pylon (e.g., in stance phase), the upper section 172 moves downward relative to the lower section 174 as shown in FIG. 15. This pulls the membrane 168 away from the housing 166, moving the pump mechanism 164 toward the expanded configuration. More particularly, the cross member 192 pulls the membrane 168 away from the closed end 184 of the cavity 180 to deform the membrane 168 between the cross member 192 and the upper section 172, increasing the volume of the fluid chamber 186.

After weight bearing or when the load is removed (e.g., in swing phase), the pump mechanism 164 returns toward the original configuration as the upper section 172 moves upward relative to the lower section 174 as shown in FIG. 14. This allows the membrane 168 to return toward the bottom 184 of the cavity 180, expelling fluid within the fluid chamber 186 out of the fluid chamber 186.

The resilient element 196 can be a biasing mechanism arranged to bias the pump mechanism 164 toward the original configuration. During weight bearing, the resilient element 196 can compress between the upper section 172 and the lower section 174. After weight bearing, the resilient element 196 can decompress and stored energy in the biasing mechanism 196 can drive the pump mechanism 164 toward the original configuration.

The connector 170 can include a lower radial flange 198 embedded in the membrane 168, an upper radial flange 202 above the membrane 168 and attached to the cross member 192, and a shaft portion 204 extending between the lower flange 198 and the upper flange 202. In some embodiments, the connector 170 may be of a two-piece construction such that the upper flange 202 can be threadedly removed from the lower flange 198 embedded in the membrane 168. The cross member 192 can define an opening for attaching the connector 170 to the cross member 192.

The pump mechanism 164 can thus generate a vacuum in a socket during stance without significantly increasing the bulk of the prosthetic device. It can also provide a dampening or shock absorbing effect to the prosthetic device.

Figure 16:
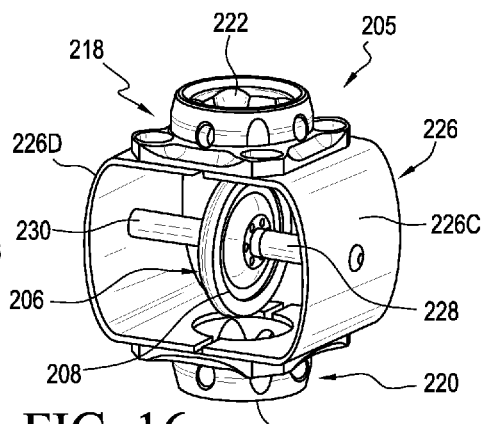
FIG. 16 shows a side isometric view of a pump system according to another embodiment.
Figure 17:
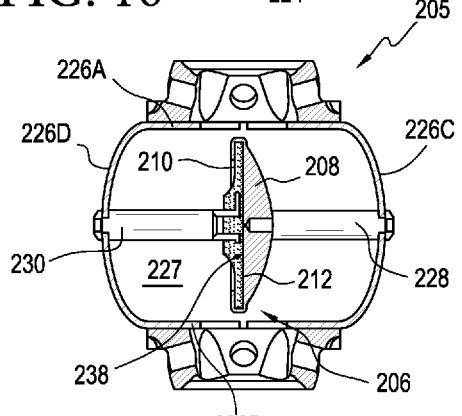
FIG. 17 shows a cross section view of the pump system in FIG. 16.
Figure 18:
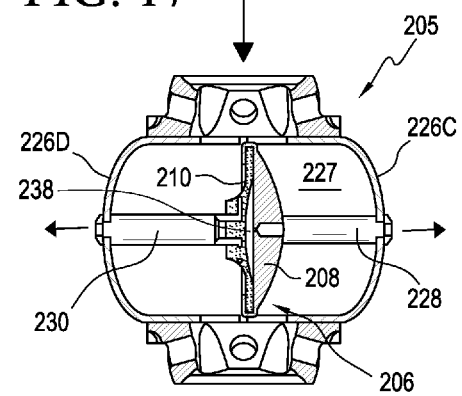
FIG. 18 shows another cross section view of the pump system in FIG. 16.

FIGS. 16-18 illustrate a pump system 205 according to another embodiment that can be integrated in an adaptor system of a prosthetic device. For instance, the pump system 205 can comprise a prosthetic connector. The pump system 205 includes a pump mechanism 206, an upper section 218, and a lower section 220. At least one of the upper and lower sections 218, 220 is arranged to move axially relative to the other. The upper section 218 can include an adaptor 222 and the lower section 220 can include an adaptor 224. The adaptors 222, 224 are shown as female adaptors but can be male adaptors or other types of prosthetic connector.

The upper section 218 can be connected to the lower section 220 via a resilient element comprising a flexible enclosure 226. The flexible enclosure 226 includes a generally horizontal top 226A attached to the upper section 218 and a generally horizontal bottom 226B attached to the lower section 220. The top and bottom 226A, 226B are connected together by convex side 226C, 226D. The top 226A, bottom 226B, and sides 226C, 226D collectively define an inner space 227 of the flexible enclosure 226. The flexible enclosure 226 can be made of a durable but flexible material such as carbon fiber cloth, unidirectional composites, plastic, and/or metal. The configuration of the flexible enclosure 226 can be adjusted based on the weight of the user and/or other factors. The flexible enclosure 226 can be formed of a single part, two parts, three parts, or any other suitable number of parts.

Similar to the other embodiments, the pump mechanism 206 can include a housing 208, a membrane 210, and one or more valve assemblies arranged to allow fluid to enter and exit the pump mechanism 206.

The pump mechanism 206 can be situated within the inner space 227 of the flexible enclosure 226. The flexible enclosure 226 can be attached to the housing 208 via a first connector 228 extending between the housing 208 and the side 226C of the flexible enclosure 226. The flexible enclosure 226 can be attached to a center portion of the membrane 210 via a second connector 230 extending between the membrane 210 and the side 226D of the flexible enclosure 226.

FIGS. 17 and 18 show cross section views of the pump mechanism 206. The pump mechanism 206 relies upon deformation of the membrane 210 to move between an original configuration (shown in FIG. 17) in which the volume of a fluid chamber 228 defined between the housing 208 and the membrane 210 is zero or near-zero, and an expanded configuration (shown in FIG. 18) in which the volume of the fluid chamber 228 is increased. The membrane 210 can be positioned in a cavity 212 of the housing 208. The housing 208 surrounds the outer radial edge portion of the membrane 210 and creates a seal with the membrane 210. The bottom of the cavity 212 can define one or more openings to form internal passageways to provide fluid communication between the fluid chamber 228 and the one or more valve assemblies.

During weight bearing or when a load is applied to the socket (e.g., in stance phase), the pump mechanism 206 moves toward the expanded configuration (shown in FIG. 18). More particularly, the upper section 218 and the lower section 220 move toward one another, which, in turn, causes the flexible enclosure 226 to compress between the upper and lower sections 218, 220. When the flexible enclosure 226 compresses, the sides 226C, 226D of the flexible enclosure 226 bow out or are forced apart, which in turn, causes at least the second connector 230 to pull the membrane 210 away from the bottom of the cavity 212, increasing the volume of the fluid chamber 228. This increase in volume of the fluid chamber 228 creates a vacuum in the pump mechanism 206, pulling fluid into the pump mechanism 206. Weight bearing on a prosthetic device thus automatically creates a vacuum in the pump mechanism 206. It will be appreciated that in other embodiments the membrane 210 can be pulled away from the bottom of the cavity 212 by the first connector 228 or the first and second connectors 228, 230 together.

After weight bearing or when the load is removed (e.g., in swing phase), the pump mechanism 206 can return toward the original configuration (shown in FIG. 17). Stored energy in the flexible enclosure 226 forces the upper and lower sections 218, 220 away from one another. This moves the first and second sides 226A, 226B back toward one another, forcing the membrane 210 toward the bottom of the cavity 212 and expel fluid within the fluid chamber 238 out of the pump mechanism 206. As such, the flexible enclosure 226 can both move the pump mechanism 206 between the original and expanded configurations when loaded, and bias the pump mechanism 206 from the expanded configuration toward the original configuration.

The pump system 205 can thus generate a vacuum in a socket in response to a load on the socket or pylon without undesirably affecting the functionality of a prosthetic foot or significantly increasing the bulk of the prosthetic device.

Figure 19:
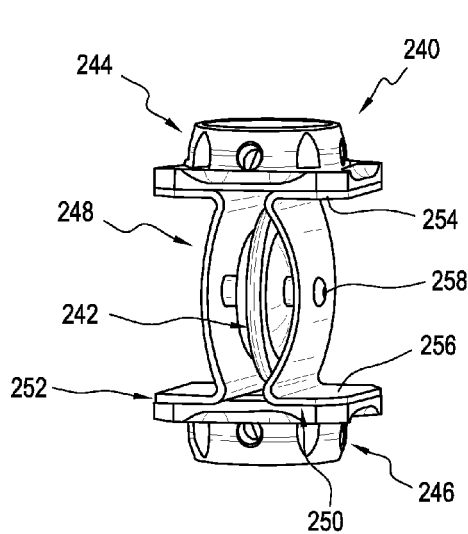
FIG. 19 shows a side isometric view of a pump system according to another embodiment.

FIG. 19 illustrates a pump system 240 according to another embodiment. It will be similar that the pump system 240 is similar in structure and function to the pump system 205 except that the flexible enclosure has a different shape. For instance, the pump system 240 includes a pump mechanism 242, an upper section 244, and a lower section 246. The upper section 244 and lower section 246 are connected to one another via a resilient element comprising a flexible enclosure 248.

In the illustrated embodiment, the flexible enclosure 248 includes a first part 250 and a second part 252 spaced from the first part 250. Each of the first and second parts 250, 252 includes a top 254 attached to the upper section 244, a bottom 256 attached to the lower section 246, and a convex intermediate segment 258 extending between the top 254 and the bottom 256. The top 254 extends radially inward from an outer edge of the upper section 244 to where it connects with the intermediate segment 258 near a middle of the upper section 244. The bottom 256 also extends radially inward from an outer edge of the lower section 246 to where it connects with the intermediate segment 258 near a middle of the lower section 246.

During weight bearing, the upper and lower sections 244, 246 move toward one another, which, in turn, causes the flexible enclosure 248 to compress. When the flexible enclosure 248 compresses, the intermediate segments 258 of the first and second parts 250, 252 bow out or are forced apart, which, in turn, moves the pump mechanism 242 toward the expanded configuration. After weight bearing, stored energy in the flexible enclosure 248 forces the upper and lower sections 244, 246 away from one another. This moves the intermediate segments 258 back toward one another, returning the pump mechanism 242 toward the original configuration.

Figure 20:
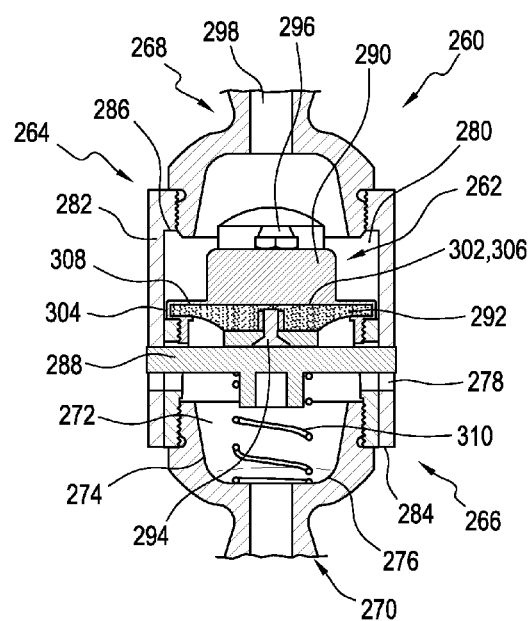
FIG. 20 shows a cross section view of a pump system according to another embodiment.
Figure 21:
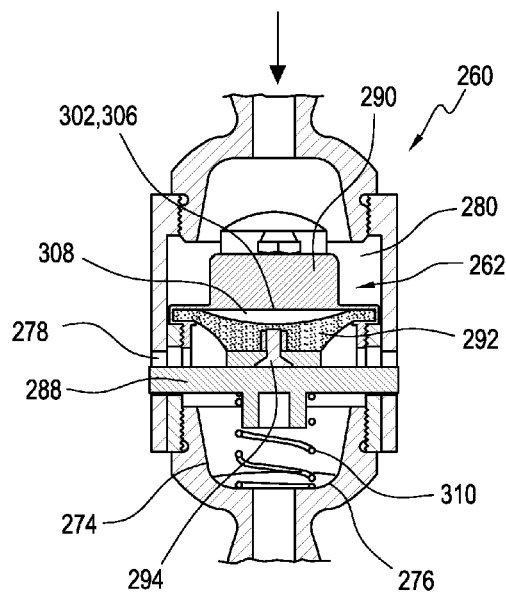
FIG. 21 shows another cross section view of the pump system in FIG. 20.

FIGS. 20 and 21 illustrate a pump system 260 according to another embodiment that can be integrated in an adaptor system of a prosthetic device. For instance, the pump system 260 can comprise a prosthetic connector. The pump system 260 includes a pump mechanism 262, an upper section 264, and a lower section 266. At least one of the upper and lower sections 264, 266 is arranged to move axially relative to the other. In the illustrated embodiment, the upper section 264 has a female configuration and the lower section 266 has a male configuration arranged to fit in the upper section 264. As seen, the upper section 264 can include an adaptor 268 and the lower section 266 can include an adaptor 270. The adaptors 268, 270 are shown as male adaptors but can be female adaptors or any other type of connector.

The lower section 266 defines a cavity 272 having a peripheral internal cavity wall 274 extending between a top opening at or near the top of the lower section 266 and a closed end 276. The cavity 272 is shown having a generally cylindrical shape but can have any suitable shape. A channel 278 extends through the lower section 266 and traverses the cavity 272.

The upper section 264 defines a cavity 280 having a peripheral internal cavity wall 282 extending between a bottom opening 284 at or near the bottom of the upper section 264 and a closed end 286. The lower section 266 is sized and configured to be received in the cavity 280 of the upper section 264. The upper section 264 includes a cross member 288 extending through the channel 278 of the lower section 266. The cross member 288 can be a pin member. The cross member 288 can extend in a generally horizontal direction. The channel 278 and the cross member 288 can be sized and configured such that the cross member 288 can move up and down within the channel 278 but also holds the upper section 264 on the lower section 266. The range of axial movement between the upper and lower sections 264, 266 can be limited by a height of the channel 278 and/or the cross member 288.

The pump mechanism 262 is positioned on the top of the lower section 266 within the cavity 280 of the upper section 264. The pump mechanism 262 includes a housing 290, a membrane 292, and a connector 294. The pump mechanism 262 may include one or more valve assemblies 296 arranged to control movement into and from the pump mechanism 262. According to a variation, a fluid passageway 298 is defined in the adaptor 268 of the upper section 264 that is fluid communication with the pump mechanism 262. This facilitates fluid entering and exiting the pump mechanism 262 to pass through the adaptor 268.

The housing 290 defines a cavity 302 provided with an undercut circumferential groove 304 between an open end of the cavity 302 and a closed end 306 of the cavity 302. An outer radial edge portion of the membrane 292 can be situated in the circumferential groove 304 such that a seal is formed between the membrane 292 and the housing 290. A center portion of the membrane 292 can be attached to the cross member 288 of the upper section 264. For instance, the connector 294 can attach the center portion of the membrane 292 to the cross member 288. The closed end 306 of the cavity 302 can define one or more openings which extend into the housing 290 to form internal passageways providing fluid communication between the one or more valve assemblies 296 and a fluid chamber defined below.

The pump mechanism 262 is movable between an original configuration (FIG. 20) in which the volume of a fluid chamber 308 defined between the top of the membrane 292 and the closed end 306 of the cavity 302 is zero or near-zero, and an expanded configuration (shown in FIG. 21) in which the volume of the fluid chamber 308 is increased.

During weight bearing or when a load is applied to a socket or pylon, the upper section 264 moves downward relative to the lower section 266 as shown in FIG. 21. This pulls the membrane 292 away from the closed end 306 of the cavity 302, moving the pump mechanism 262 toward the expanded configuration. More particularly, the cross member 288 of the upper section 264 moves downward within the channel 278 and pulls the center portion of the membrane 282 away from the closed end 306 of the cavity 302 to deform the membrane 282, increasing the volume of the fluid chamber 308.

After weight bearing or when the load is removed, the pump mechanism 262 can return toward the original configuration as the upper section 264 and cross member 288 move upward relative to the lower section 266 as shown in FIG. 20. This allows the membrane 292 to return towards the closed end 306 of the cavity 302, expelling fluid within the fluid chamber 308.

According to a variation, the pump system 260 can include a biasing mechanism 310 arranged to bias the pump mechanism 262 toward the original configuration. The biasing mechanism 310 can comprise a spring member disposed between the closed end 276 of the lower section 266 and the cross member 288 of the upper section 264. In an embodiment, the spring member can be positioned on a stem portion extending downwardly from the cross member 288. When the pump system 260 is loaded, the biasing mechanism 310 can compress between the closed end 276 of the lower section 266 and the cross member 288 of the upper section 264. When the pump system 260 is unloaded, the biasing mechanism 310 can decompress and stored energy in the biasing mechanism 310 can drive the pump mechanism 260 toward the original configuration.

According to a variation, the housing 290 can be threadedly attached to the lower section 266. For instance, the housing 290 can define a plurality of external threads arranged to mesh with a plurality of internal threads defined by the lower section 266. In an embodiment, the adaptor portion 268 can be threadedly attached to the upper section 264 and the adaptor portion 270 can be threadedly attached to the lower portion 266.

Figure 22:
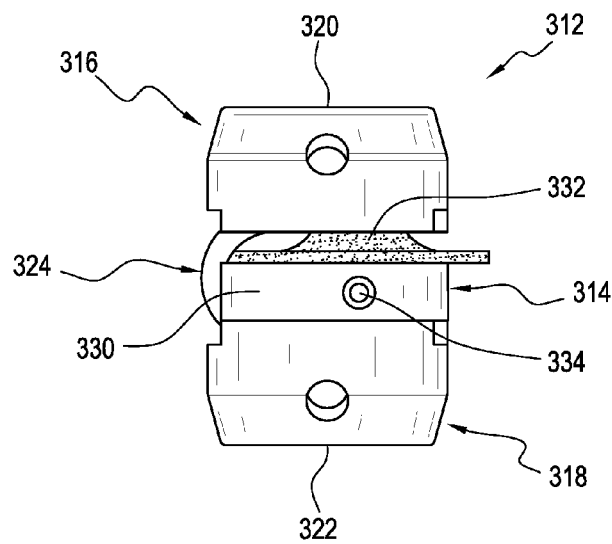
FIG. 22 shows a side view of a pump system according to another embodiment.
Figures 23, 24:
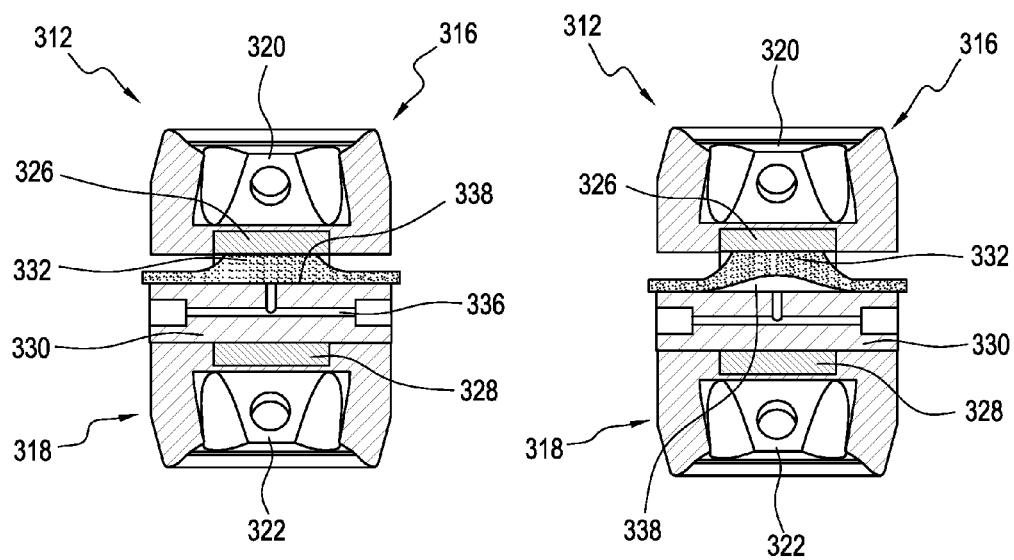
FIG. 23 shows a cross section view of the pump system in FIG. 22.
FIG. 24 shows another cross section view of the pump system in FIG. 22.

FIGS. 22-24 illustrate a pump system 312 according to another embodiment that can be integrated in an adaptor system of a prosthetic device. In an embodiment, the pump system 312 can comprise a prosthetic connector. The pump system 312 includes a pump mechanism 314, an upper section 316, and a lower section 318. At least one of the upper and lower sections 316, 318 is arranged to move relative to the other. In an embodiment, the upper section 316 includes an adaptor 320 and the lower section 318 includes an adaptor 322. The adaptors 320, 322 are shown as female adaptors but can be male adaptors or any other suitable connectors.

A resilient element 324 connects the upper section 316 and the lower section 318. The resilient element 324 can be any suitable member but is shown as a blade having a semicircular configuration with an upper arm 326 attached to the upper section 316 and a lower arm 328 attached to the lower section 318.

The pump mechanism 314 is positioned between the upper and lower sections 316, 318. The pump mechanism 314 includes a housing 330 and a membrane 332. The pump mechanism 314 may include one or more valve assemblies 334 arranged to control movement of fluid into and from the pump mechanism 314. The housing 330 defines an internal passageway 336 providing fluid communication between the one or more valve assemblies 334.

An outer edge portion of the membrane 332 is attached to the housing 330 such that a seal is formed between the membrane 332 and the housing 330. A center portion of the membrane 332 can be attached to the upper arm 326 of the resilient element 324.

The pump mechanism 314 is movable between an original configuration (shown in FIG. 23) in which the volume of a fluid chamber 338 defined between the bottom of the membrane 332 and the housing 330 is zero or near-zero, and an expanded configuration (shown in FIG. 24) in which the volume of the fluid chamber 338 is increased.

During moment or rotation of the upper and lower sections 316, 318 away from one another (e.g., after heel strike), the pump mechanism 314 moves toward the expanded configuration. More particularly, the upper arm 326 of the resilient element 324 pulls the center portion of the membrane 332 away from the housing 330, increasing the volume of the fluid chamber 338. This increase in volume of the fluid chamber 338 creates a vacuum in the pump mechanism 314, pulling fluid into pump mechanism 314 through the one or more valve assemblies 334.

During moment or rotation of the upper and lower sections 316, 318 toward one another, the pump mechanism 314 moves toward the original configuration. More particular, the resilient element 324 forces the pump mechanism 314 toward the original configuration and decreases the volume of the fluid chamber 338. During the return of the membrane 332 toward the housing 330, the pump mechanism 314 expels fluid in the fluid chamber 338 out of the one or more valve assemblies 334.

Figure 25:
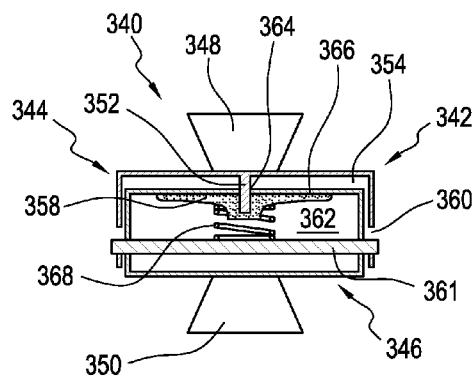
FIG. 25 shows a cross section view of a pump system according to another embodiment.
Figure 26:
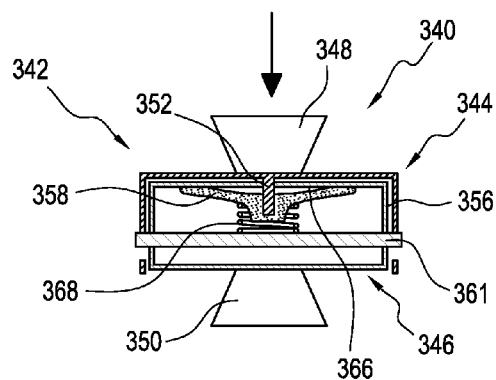
FIG. 26 shows another cross section view of the pump system in FIG. 25.

FIGS. 25 and 26 illustrate a pump system 340 according to another embodiment that can be integrated in an adaptor system of a prosthetic device. As seen, the pump system 340 can comprise a prosthetic connector. The pump system 340 includes a pump mechanism 342, an upper section 344, and a lower section 346. The upper section 344 is arranged to move axially relative to the pump mechanism 342 and the lower section 346. According to a variation, the upper section 344 includes an adaptor 348 and the lower section 346 includes an adaptor 350. The adaptors 348, 350 are shown as male adaptors but can be female adaptors or any other suitable connectors. The upper section 344 includes a pin member 352 extending in a downward direction and a through-hole 360. A horizontal member 361 attached to the lower section 346 and protrudes through the through-hole 360 of the upper section 344 to help maintain the upper section 344 on the lower section 346. The through-hole 360 and the horizontal member 361 can be sized and configured such that the horizontal member 361 can move up and down within the through-hole 360.

The pump mechanism 342 is attached to an upper surface of the lower section 346 and positioned within an open cavity 354 defined by the upper section 344. The pump mechanism 342 includes a housing 356 and a membrane 358. The pump mechanism 342 may include one or more valve assemblies similar to the other embodiments arranged to control movement of fluid into and from the pump mechanism 342. The housing 356 can define passageways providing fluid communication between the one or more valve assemblies.

The housing 356 can define an internal chamber 362 and through opening 364 arranged to allow the pin member 352 to pass therethrough. The membrane 358 is disposed in the internal chamber 362. An outer edge of the membrane 358 of the membrane 358 is attached to the upper internal wall of the internal chamber 362. A center portion of the membrane 358 can be attached to the pin member 352.

The pump mechanism 342 is movable between an original configuration (shown in FIG. 25) in which the volume of a fluid chamber 366 defined between the top of the membrane 358 and the housing 356 is zero or near-zero, and an expanded configuration (shown in FIG. 26) in which the volume of the fluid chamber 366 is increased.

During weight bearing or when a load is applied to a socket or pylon, the upper section 344 moves downward relative to the lower section 346, which, in turn, causes the pin member 352 to push the center portion of the membrane 358 away from the upper internal wall of the internal chamber 362, increasing the volume of the fluid chamber 366. This increase in volume of the fluid chamber 366 creates a vacuum in the pump mechanism 342, pulling fluid into the pump mechanism 342. Weight bearing on a prosthetic device thus automatically creates a vacuum in the pump mechanism 342.

After weight bearing, the pump mechanism 342 returns toward the original configuration as the upper section 344 moves upward relative to the lower section 346. This moves the pin member 352 in the upward direction, pulling the membrane 358 toward the upper internal wall of the internal chamber 362 and expelling fluid within the fluid chamber 366 out of the pump assembly 342.

According to a variation, the pump system 340 can include a biasing mechanism 368 arranged to bias the pump mechanism 342 toward the original configuration. The biasing mechanism 368 can comprise a spring member positioned between the bottom of the membrane 358 and the bottom of the internal chamber 362. During weight bearing, the biasing mechanism 368 can compress between the membrane 358 and the bottom of the housing 356. After weight bearing, the biasing mechanism 368 can decompress and stored energy in the biasing mechanism 368 can drive the pump mechanism 342 toward the original configuration.

The pump mechanism 342 can thus generate a vacuum in a socket during stance without undesirably affecting the functionality of the prosthetic foot or significantly increasing the bulk of the prosthetic device. In addition, the pump mechanism 342 can advantageously provide a dampening or shock absorbing effect to the prosthetic device, allowing for a more comfortable gait cycle.

Figure 27:
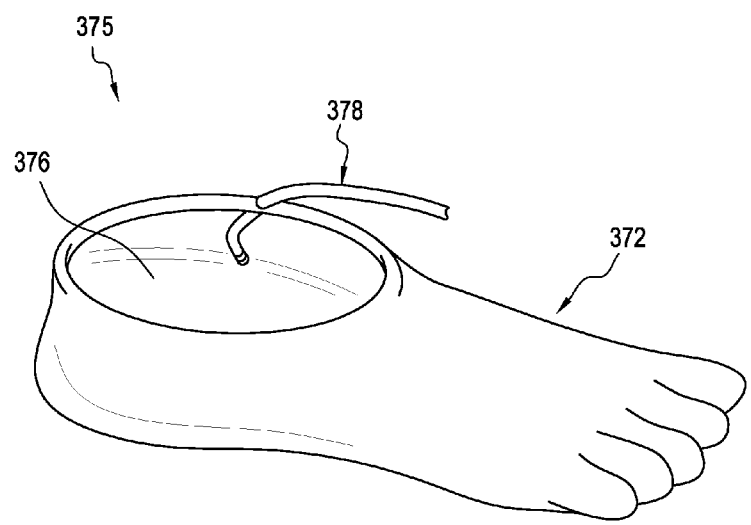
FIG. 27 shows a side isometric view of a vacuum suspension system according to another embodiment.
Figure 28:
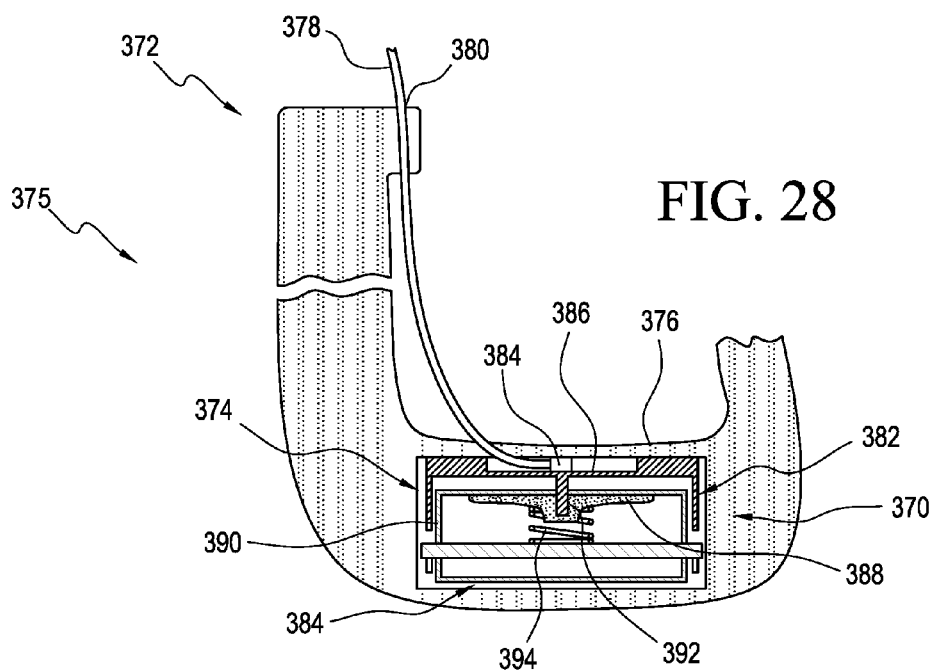
FIG. 28 is a cross section view of the vacuum suspension system in FIG. 27.

FIGS. 27 and 28 show a vacuum suspension system 375 comprising a pump system 370 and a foot cover 372 according to another embodiment. The pump system 370 can include a pump mechanism 374 (shown in FIG. 28) disposed in a heel portion 376 of the foot cover 372 and a tube system 378 integrated with the foot cover 372. The tube system 378 is in fluid communication with the pump mechanism 374 and a socket. In an embodiment, the tube system 378 can extend from the heel portion 376 and through a hole 380 formed in a top portion of the foot cover 372 defining a foot opening of the foot cover 372.

FIG. 28 is a cross section view of the vacuum suspension system 375. The pump system 370 can be similar to the pump system 340 except the upper and lower sections 382, 384 do not include adaptors. As seen, the pump mechanism 374 utilizes the space within the body of the foot cover 372 such that it does not add any additional volume to the prosthetic device or the foot cover 372. In addition, the pump mechanism 374 can easily retrofit to existing foot covers and can be formed to be used with right or left foot covers. In addition, because the pump system 370 is formed within a thickness of the foot cover 372, it reduces the likelihood of the pump system 370 undesirably affecting the functionality of a prosthetic foot, providing a more natural gait.

The pump mechanism 374 can be in fluid communication with one or more valve assemblies 384 associated with the tube system 378. Similar to the other embodiments, the one or more valve assemblies 384 are arranged to control fluid flow into and out of the pump mechanism 374.

The pump mechanism 374 is movable between an original configuration in which the volume of a fluid chamber 386 defined between a membrane 388 and a housing 390 is zero or near-zero, and an expanded configuration in which the volume of the fluid chamber 386 is increased.

During gait or when a load is applied to the foot cover 372, the upper section 382 moves downward relative to the lower section 384, which, in turn, causes a pin member 392 to push the center portion of the membrane 388 away from the housing 390, increasing the volume of the fluid chamber 386. This increase in volume of the fluid chamber 386 creates a vacuum in the pump mechanism 374, pulling fluid into the pump mechanism 374. Weight bearing during gait thus automatically creates a vacuum in the pump mechanism 374.

After weight bearing, the pump mechanism 374 returns toward the original configuration as the upper section 382 moves upward relative to the lower section 384. This moves the pin member 392 in the upward direction, pulling the membrane 388 toward the upper wall of the housing 290 and expelling fluid within the fluid chamber 386 out of the pump assembly 374.

According to a variation, the pump system 370 can include a biasing mechanism 394 arranged to bias the pump mechanism 374 toward the original configuration. The prosthetic device thus automatically creates a vacuum in the pump mechanism 374 during stance and automatically expels fluid to atmosphere during the swing phase.

Figure 29:
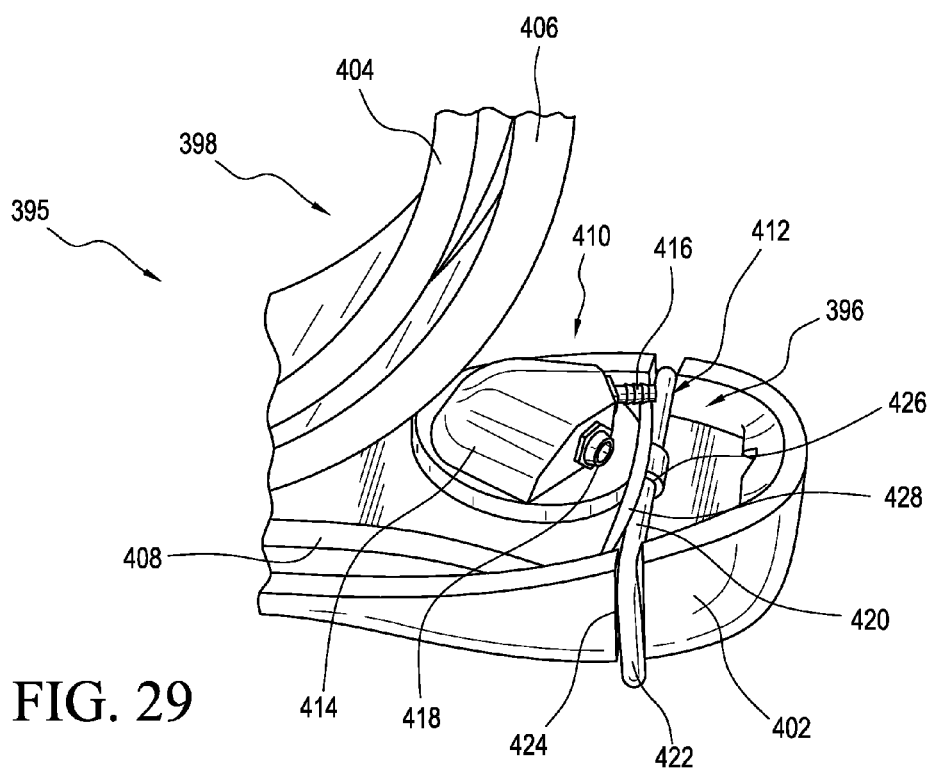
FIG. 29 shows a partial side isometric view of a vacuum suspension system according to another embodiment.

While the pump system is generally described as being separate from a prosthetic foot, in other embodiments, the pump system can be adapted to be located on the prosthetic foot. For instance, FIG. 29 shows a vacuum suspension system 395 comprising a pump system 396, a prosthetic foot 398, and a foot cover 402 according to another embodiment.

The prosthetic foot 398 has an upper foot member 404 and a lower foot member 406, which is disposed generally below the upper foot member 404. The prosthetic foot 398 can have a heel member 408 that extends rearwardly to a free end and is disposed below at least a portion of the lower foot member 406. The prosthetic foot 398 may be insertable into the foot cover 402 as seen. In use, the prosthetic foot 398 can expand and compress.

The pump system 396 includes a pump mechanism 410 that is operable between the heel member 408 and a support member 412 coupled to the foot cover 402. The pump mechanism 410 can be positioned in the space between the heel member 408 and the bottom surface of the lower foot member 406, making it unlikely that the pump mechanism 410 will negatively affect the functionality of the prosthetic foot 398. Further, the pump mechanism 410 can be formed to be used with both left and right prosthetic feet.

Similar to the other embodiments, the pump mechanism 410 includes a housing 414 containing two one-way valve assemblies 416, 418, a membrane, and a connector. The valve assembly 416 only allows fluid to enter the pump mechanism 410 which can be in fluid communication with the cavity of a socket. The valve assembly 418 only allows fluid to be expelled out of the pump mechanism 410, preferably to atmosphere. The connector can be attached to the membrane and the heel member and can exhibit any suitable configuration. For instance, the connector may be a single fastener or screw, allowing the pump mechanism 410 to easily retrofit on a prosthetic foot. The housing 414 can be attached to the support member 412.

Similar to the previously described pump mechanisms, the pump mechanism 410 relies upon deformation of the membrane to move between an original configuration in which the volume of a fluid chamber defined between an upper surface of the membrane and the bottom of the housing 414 is zero or near-zero, and an expanded configuration in which the volume of the fluid chamber is increased.

The housing 414 is arranged to surround the outer radial edge portion of the membrane and creates a seal with the membrane. The bottom of the housing 414 defines a pair of openings which extend into the housing 414 to form internal passageways to provide fluid communication between the fluid chamber and the two one-way valve assemblies 416, 418.

The support member 412 can be coupled to the foot cover 402. The support member 412 can be any suitable member but is shown as a metal rod having a cross member 420 extending in a transverse direction across the foot cover 402 above the heel member 408 and side members 422 extending downwardly along the sides of the foot cover 402 toward the ground. According to a variation, the foot cover 402 can include one or more reinforcements where the side members 422 extend along the sides of the foot cover 402. The outer surface of the foot cover 402 can define slots 424 to receive the side members 422 of the support member 412, helping to maintain the position of the support member 412 on the foot cover 402. This also lowers the profile of the support member 412, reducing the likelihood of the support member 412 interfering with footwear.

The support member 412 can be pivotally connected to the housing 414. For instance, the cross member 420 of the support member 412 can extend through a channel or hole 426 defined by the housing 414 such that the housing 414 is pivotally connected to the support member 412.

Upon heel strike, the prosthetic foot 398 moves into expansion, which, in turn, causes the heel member 408 and the cross member 420 of the support member 412 to move apart. This separation causes the housing 414 to pivot around the cross member 420, which, in turn, rotates the housing 414 away from the heel member 408.

As the housing 414 rotates away from the heel member 408, the heel member 408 pulls the membrane away from the housing 414, increasing the volume of the fluid chamber. This increase in volume of the fluid chamber creates a vacuum in the pump mechanism 410, pulling fluid into the pump mechanism 410 through the valve assembly 104. Expansion of the prosthetic foot thus automatically creates a vacuum in the pump mechanism 410.

As the prosthetic foot 398 moves from heel strike through mid-stance and/or toe-off, the prosthetic foot 398 moves into compression. In compression, the heel member 408 and the cross member 420 of the support member 412 move toward one another, which, in turn, forces the pump mechanism 410 back toward its original configuration and decreases the volume of the fluid chamber to a zero or near-zero volume.

During the return of the membrane toward the housing 414, the pump mechanism 410 expels fluid in the fluid chamber out of the valve assembly 424. Because the pump mechanism 410 returns to its original configuration of zero or near-zero volume in the fluid chamber at mid-stance and/or toe-off, all fluid drawn into the pump mechanism 410 can be automatically expelled rather than relying on complete compression cycle of the pump to expel air drawn in from the socket as in the prior art.

According to a variation, the pump system 396 can include a biasing mechanism 428 arranged to help the pump mechanism 410 return to its configuration. For instance, at least one band member having an elastomeric configuration can extend around the heel member 408 and the housing 414, biasing the housing 414 toward the heel member 408 and/or biasing the support member 412 and the foot cover 402 together.

It will be appreciated that the prosthetic devices described herein are to be regarded as exemplary only, as any prosthetic device is possible. For instance, while the valve assemblies are described being attached to the housing, in other embodiments, one or more of the valve assemblies can be in fluid communication with the pump mechanism via a tubular fluid conduit. It will be appreciated that the housing can be made of any suitable material such as carbon fiber cloth, unidirectional composites, plastic, or metal. It will be appreciated that embodiments of the pump system described herein can include at least one sensor (e.g., a Hall Effect Sensor or gap-sensor) arranged to measure one or more relationships such as displacement or force between two components of the pump system. For instance, the at least one sensor can be incorporated in the upper section 268 and/or the lower section 270 of the pump system 260. Output from the at least one sensor can be used to regulate pressure in a socket, for general sensory feedback information on gait and performance characteristics, or for another suitable purpose.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A vacuum suspension system comprising:
   a pump system arranged to be in fluid communication with a prosthetic socket, the pump system including a pump mechanism comprising a prosthetic connector adapted to form at least part of a load bearing connection between a prosthetic foot and the prosthetic socket, the pump mechanism comprising:
   upper and lower sections arranged to move relative to one another, the upper section defining a pin member;
   a housing positioned between the er and lower sections, the housing defining an opening arranged to allow the pin member to slidably pass therethrough; and
   a membrane situated on the housing such that a fluid chamber is defined between an upper side of the membrane and the housing, the pump mechanism movable between an original configuration in which the volume of the fluid chamber is zero or near-zero, and an expanded configuration in which the upper section moves toward the housing and the pin member is engageable with the upper side of the membrane and selectively deforms the membrane to increase the volume of the fluid chamber when the pump system is loaded in stance.

2. The vacuum suspension system of claim 1, wherein the upper section defines a cavity receiving the lower section.

3. The vacuum suspension system of claim 1, wherein the upper and lower sections arranged to move in an axial direction relative to one another.

4. The vacuum suspension system of claim 1, wherein the lower section defines a cavity arranged to receive the membrane.

5. The vacuum suspension system of claim 1, wherein the membrane is positioned between the lower section and the housing.

6. The vacuum suspension system of claim 1, wherein the prosthetic connector is in axial alignment with a pylon extending between the prosthetic foot and the socket.

7. The vacuum suspension system of claim 1, wherein the upper section includes a female adaptor or a male adaptor.

8. The vacuum suspension system of claim 1, wherein the upper section is connected to the lower section via a resilient element.

9. The vacuum suspension system of claim 8, wherein the resilient element comprises a flexible enclosure.

10. A vacuum suspension system comprising:
    a prosthetic socket; and
    a pump system arranged to be in fluid communication with a prosthetic socket, the pump system including a pump mechanism comprising a prosthetic connector adapted to form at least part of a load bearing connection between a prosthetic foot and the prosthetic socket, the pump mechanism comprising:
    upper and lower sections arranged to move relative to one another, the upper section defining a pin member;
    a housing positioned between the upper and lower sections, the housing defining an opening arranged to allow the pin member to slidably pass therethrough; and
    a membrane situated on the housing such that a fluid chamber is defined between an upper side of the membrane and the housing, the pump mechanism movable between an original configuration in which the volume of the fluid chamber is zero or near-zero, and an expanded configuration in which the upper section moves toward the housing and the pin member is engageable with the upper side of the membrane and selectively deforms the membrane to increase the volume of the fluid chamber when the pump system is loaded in stance.

11. The vacuum suspension system of claim 10, wherein the lower section is receiving within the upper section.

12. The vacuum suspension system of claim 10, wherein the housing is attached to the lower section.

13. The vacuum suspension system of claim 10, wherein the membrane is positioned between the lower section and the housing.

14. The vacuum suspension system of claim 10, wherein the lower section defines a female adaptor.

* * * * *